(12) United States Patent
McIntyre et al.

(10) Patent No.: US 11,904,144 B2
(45) Date of Patent: Feb. 20, 2024

(54) DEVICES AND METHODS FOR MAKING THERAPEUTIC FLUIDS

(71) Applicant: ARTHREX, INC., Naples, FL (US)

(72) Inventors: Hannah McIntyre, Naples, FL (US);
Christopher Bare, Naples, FL (US);
Andrea Matuska, Naples, FL (US);
Samantha Pellegrino, Naples, FL (US);
Jerome Gulvas, Naples, FL (US)

(73) Assignee: Arthrex, Inc., Naples, FL (US)

( * ) Notice: Subject to any disclaimer, the term of this patent is extended or adjusted under 35 U.S.C. 154(b) by 573 days.

(21) Appl. No.: 17/062,036

(22) Filed: Oct. 2, 2020

(65) Prior Publication Data

US 2021/0100957 A1     Apr. 8, 2021

Related U.S. Application Data

(60) Provisional application No. 62/910,794, filed on Oct. 4, 2019.

(51) Int. Cl.
*A61M 5/315*     (2006.01)
*A61M 5/31*      (2006.01)
*A61M 5/19*      (2006.01)

(52) U.S. Cl.
CPC .......... *A61M 5/31501* (2013.01); *A61M 5/19* (2013.01); *A61M 5/3148* (2013.01);
(Continued)

(58) Field of Classification Search
CPC ............ A61M 5/31501; A61M 5/3148; A61M 5/31525; A61M 5/31535; A61M 5/31576; A61M 5/31511; A61M 2005/31506; A61M 5/31505; A61M 5/19; A61M 5/3135; A61M 2005/31598; A61M 1/185; A61M 1/67; A61M 1/029; A61M 1/382; A61M 2202/10; A61M 1/3693; A61M 2202/0427;
(Continued)

(56) References Cited

U.S. PATENT DOCUMENTS 1,770,633 A * 7/1930 Smith ............... A61M 5/24
604/234
2,369,304 A * 2/1945 Lewis ............ A61B 5/150519
604/209
(Continued)

FOREIGN PATENT DOCUMENTS

CA      2617465 A1    7/2009
EP      0208975 A2    1/1987
(Continued)

OTHER PUBLICATIONS

Song et al, "Comparison of the efficacy of bone marrow mononuclear cells and bone mesenchymal stem cells in the treatment of osteoarthritis in a sheep model", Int J Clin Pathol., vol. 7, No. 4, pp. 1415-1426, (2014).
(Continued)

*Primary Examiner* — Brandy S Lee
*Assistant Examiner* — Hong-Van N Trinh
(74) *Attorney, Agent, or Firm* — Lathrop GPM LLP; Lisa Hillman

(57) ABSTRACT

Devices and methods for extracting and concentrating therapeutically active factors from mammalian fluids and tissues are described herein.

12 Claims, 29 Drawing Sheets

(52) U.S. Cl.
CPC .... *A61M 5/31511* (2013.01); *A61M 5/31525* (2013.01); *A61M 5/31535* (2013.01); *A61M 5/31576* (2013.01); *A61M 2005/3128* (2013.01)

(58) Field of Classification Search
CPC .. A61M 2202/0437; A61M 2202/0415; A61M 2005/2418; A61M 2005/2437; A61M 2005/2485; A61M 2005/5033; A61M 5/2422; A61B 5/15003; A61B 5/150236; A61B 5/150244; A61B 5/150251; A61B 5/150267; A61B 5/150755; A61B 5/153; A61B 5/15
See application file for complete search history.

(56) References Cited

U.S. PATENT DOCUMENTS

| | | | |
|---|---|---|---|
| 4,906,231 A * | 3/1990 | Young | A61M 5/5013 604/110 |
| 5,084,017 A * | 1/1992 | Maffetone | A61M 5/5066 604/110 |
| 5,250,030 A * | 10/1993 | Corsich | A61M 5/5013 604/218 |
| 5,328,476 A * | 7/1994 | Bidwell | A61M 5/5013 604/218 |
| 6,649,072 B2 | 11/2003 | Brandt et al. | |
| 6,716,187 B1 | 4/2004 | Jorgensen et al. | |
| 7,452,344 B2 | 11/2008 | Jorgensen et al. | |
| 7,927,563 B1 | 9/2011 | Lavi | |
| 8,052,969 B2 | 11/2011 | Buhr et al. | |
| 8,950,586 B2 | 2/2015 | Dorian et al. | |
| 9,050,403 B2 | 6/2015 | Morimoto et al. | |
| 9,101,688 B2 | 8/2015 | Teets et al. | |
| 9,205,110 B2 | 12/2015 | Bare | |
| 9,241,977 B2 | 1/2016 | Bare et al. | |
| 9,248,238 B2 * | 2/2016 | Shovary | A61M 5/31501 |
| 9,329,165 B2 | 5/2016 | Ihm et al. | |
| 9,555,171 B2 | 1/2017 | Sengun et al. | |
| 9,693,789 B2 * | 7/2017 | Garrison | A61M 5/3129 |
| 9,718,003 B1 | 8/2017 | Petrie | |
| 9,757,506 B2 | 9/2017 | Ra et al. | |
| 9,804,070 B2 | 10/2017 | Hassouneh et al. | |
| 10,040,064 B1 | 8/2018 | Petrie | |
| 10,058,799 B2 | 8/2018 | Lee | |
| 10,512,659 B2 | 12/2019 | Tucker et al. | |
| 2006/0273050 A1 | 12/2006 | Higgins et al. | |
| 2007/0049872 A1 | 3/2007 | Watts et al. | |
| 2008/0021391 A1 * | 1/2008 | Polidoro | A61M 5/5013 604/110 |
| 2008/0166421 A1 | 7/2008 | Buhr et al. | |
| 2011/0077596 A1 | 3/2011 | Higgins et al. | |
| 2012/0015796 A1 | 1/2012 | Leach et al. | |
| 2012/0237490 A1 | 9/2012 | Karli et al. | |
| 2014/0010857 A1 | 1/2014 | Turzi et al. | |
| 2014/0097135 A1 | 4/2014 | Leach et al. | |
| 2014/0272925 A1 | 9/2014 | Menon et al. | |
| 2014/0276592 A1 | 9/2014 | Mottola et al. | |
| 2014/0343511 A1 * | 11/2014 | Grunhut | A61M 5/31515 604/227 |
| 2015/0064687 A1 | 3/2015 | Nemirovsky | |
| 2015/0073356 A1 | 3/2015 | Sasayama et al. | |
| 2015/0105754 A1 * | 4/2015 | Roche | A61M 1/67 604/542 |
| 2015/0209502 A1 | 7/2015 | Bare | |
| 2015/0328388 A1 | 11/2015 | Okamoto et al. | |
| 2016/0008808 A1 | 1/2016 | Levine et al. | |
| 2017/0028137 A1 | 2/2017 | Mirabito et al. | |
| 2017/0144173 A1 | 5/2017 | Sengun et al. | |
| 2017/0182254 A1 * | 6/2017 | Heinsbergen | A61M 5/31511 |
| 2018/0106706 A1 | 4/2018 | Hassouneh et al. | |
| 2018/0120206 A1 | 5/2018 | Hassouneh et al. | |
| 2018/0264199 A1 | 9/2018 | Mirabito et al. | |

FOREIGN PATENT DOCUMENTS

| | | |
|---|---|---|
| EP | 2823832 A1 | 1/2015 |
| EP | 3175874 B1 | 6/2017 |
| EP | 3316780 A1 | 5/2018 |
| WO | 2013140858 A1 | 9/2013 |
| WO | 2016179280 A1 | 11/2016 |
| WO | 2017093838 A1 | 6/2017 |

OTHER PUBLICATIONS

Rodriguez et al, "Autologous Stromal vascular fraction therapy for rheumatoid arthritis: rationale and clinical safety", International Archives of Medicine, vol. 5, No. 5, pp. 1-9, (2012).

Sampson et al, "Platelet rich plasma injection grafts for musculoskeletal injuries: a review", Current Reviews in Musculoskeletal Medicine, vol. 1, No. 3-4, pp. 165-174, Dec. 1, 2008.

Simari et al, "Bone marrow mononuclear cell therapy for acute myocardial infarction: A perspective from the cardiovascular cell therapy research network", Circulation Research, vol. 114, pp. 1564-1568, (2014).

EP Application No. 20199198.1, Office Action dated Apr. 26, 2023, 7 pages.

* cited by examiner

DEVICES AND METHODS FOR MAKING THERAPEUTIC FLUIDS

PRIORITY

This application claims the benefit of U.S. Ser. No. 62/910,794, filed on Oct. 4, 2019, which is incorporated by reference in its entirety.

BACKGROUND

Devices and methods for extracting and concentrating therapeutically active factors from mammalian tissues are disclosed herein. Therapeutic fluid and compositions with enhanced concentrations of therapeutically active factors can be used in the treatment of mammalian injuries or diseases.

SUMMARY OF THE DISCLOSURE

Therapeutic factors, including growth factors, cytokines, certain proteins, and viable cells which can produce the aforementioned are useful for treating damaged mammalian tissue. Therapeutic factors can be found in mammalian fluids. These therapeutic factors can be concentrated by methods known in the art. However, these methods risk contamination of the sample in addition to being challenging and inefficient to execute. There is thus a need for improved devices and methods for extracting and concentrating therapeutically active factors from mammalian tissues.

In an embodiment, a device for controlling the movement of a syringe plunger includes:
  a locking support cage comprising
    a tubular body having an aperture that is configured to surround a syringe, and
    at least one ridge disposed on an outer surface of the tubular body; and
  a locking clip configured to surround the locking cage and wherein the locking clip comprises an inner surface configured to interact with the at least one ridge so as to prevent regression of the syringe plunger during extension.

In an embodiment, a device for controlled positioning of a syringe plunger can include:
  a) a first syringe having a first body with a first diameter;
  b) a second syringe nested within the first syringe, wherein the second syringe comprises a second body with a second diameter smaller than the first diameter;
  c) a plunger nested within the second body;
  d) a locking support cage comprising:
    a tubular body having an aperture, and at least one ridge disposed on an outer surface of the tubular body, wherein the locking support cage surrounds the second syringe; and
  e) a locking clip configured i) to surround the locking cage and be fastened around finger grips of the first syringe, and ii) to interact with the at least one ridge of the locking cage via an inner surface so as to prevent regression of the plunger during extension.

In another embodiment, a device for controlled positioning of a syringe plunger can include:
  a) a first syringe having a first body with a first diameter;
  b) a second syringe having a second body with a second diameter smaller than the first diameter nested within the first syringe;
  c) a third syringe having a third body with a third diameter smaller than the second diameter nested within the second syringe;
  d) a plunger nested within the third body;
  e) a locking support cage comprising:
    a tubular body having an aperture, and
    at least one ridge disposed on an outer surface of the tubular body,
    wherein the locking support cage surrounds the second syringe; and
  f) a locking clip configured i) to surround the locking cage and to be fastened around the finger grips of the first syringe, and ii) to interact with the at least one ridge of the locking cage via an inner surface so as to prevent regression of the plunger during extension.

In an embodiment a method of obtaining a therapeutic fluid can include introducing a biological fluid such as bone marrow aspirate or whole blood into a first syringe of a device for controlled positioning of a syringe plunger, said device comprising:
  a first syringe having a first body with a first diameter;
  a second syringe having a second body with a second diameter smaller than the first diameter nested within the first syringe;
  a plunger nested within the second body;
  a locking support cage comprising:
    a tubular body having an aperture, and
    at least one ridge disposed on an outer surface of the tubular body,
    wherein the locking support cage surrounds the second syringe; and
  a locking clip configured to surround the locking cage and to be fastened around the finger grips of the first syringe, wherein the locking clip comprises an inner surface configured to interact with the at least one ridge of the locking cage so as to prevent regression of the plunger during extension; and
  centrifuging the syringe assembly to obtain a therapeutic fluid.

In another embodiment a method of obtaining a therapeutic fluid can include: introducing a biological fluid such as bone marrow aspirate or whole blood into a first syringe of a device for controlled positioning of a syringe plunger, said device comprising:
  a first syringe having a first body with a first diameter;
  a second syringe having a second body with a second diameter smaller than the first diameter nested within the first syringe;
  a third syringe having a third body with a third diameter smaller than the second diameter nested within the second syringe;
  a plunger nested within the third body;
  a locking support cage comprising a tubular body having an aperture, and at least one ridge disposed on an outer surface of the tubular body, wherein the locking support cage surrounds the second syringe; and
  a locking clip configured to surround the locking cage and be fastened around the finger grips of the first syringe, wherein the locking clip comprises an inner surface configured to interact with the at least one ridge of the locking cage so as to prevent regression of the plunger during extension;
  and centrifuging the syringe assembly to obtain a therapeutic fluid.

A method can also include disconnecting the innermost syringe (the second or third syringe) containing therapeutic fluid from any other syringes and applying the therapeutic fluid to tissue.

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure, and together with the description serve to explain the principles and operation of the disclosure.

DETAILED DESCRIPTION

Figure 1:
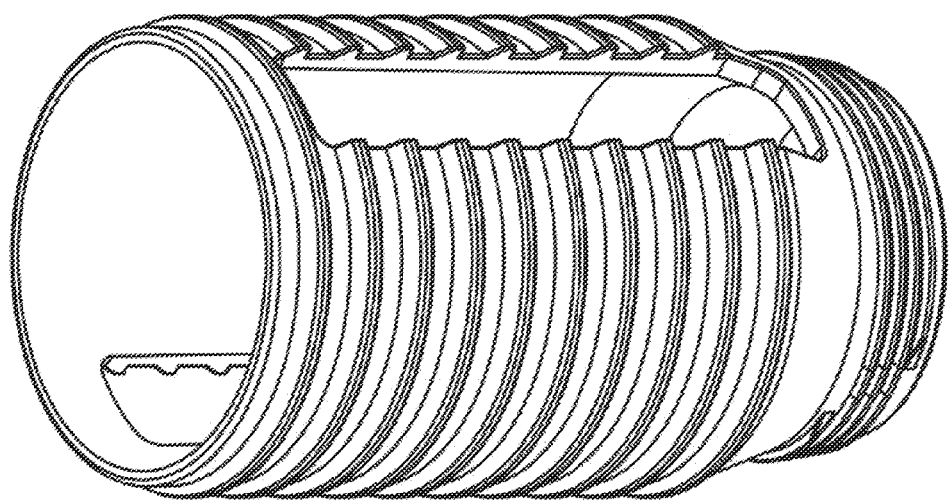
FIG. 1 illustrates a perspective view of a locking cage of a device for controlling the movement of a syringe plunger.
Figure 2:
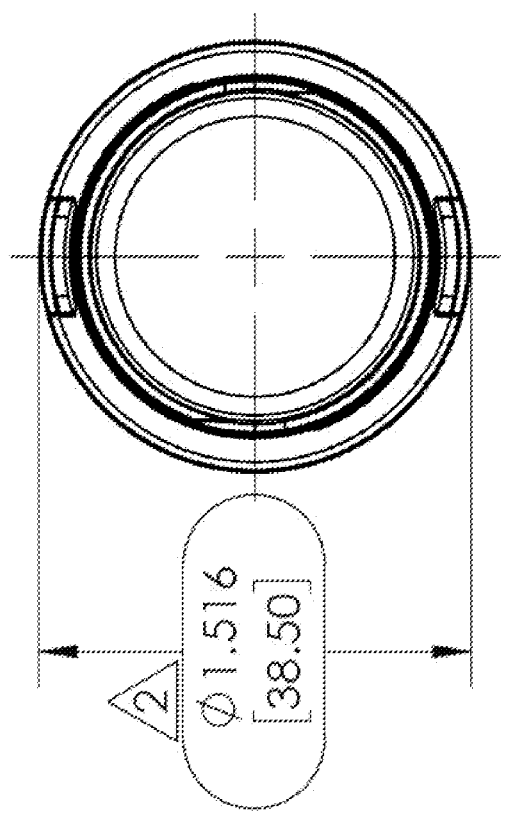
FIG. 2 illustrates a top view of a locking cage of a device for controlling movement of a syringe plunger.

A locking support cage and locking clip device, as well as a multi-syringe, locking support cage, and locking clip devices described herein provide a removable and reusable plunger locking mechanism to aid in, for example, biological fluid. A locking support cage and locking clip are configured such that a plunger can be pulled out, but not pushed back in, maintaining a vacuum within the syringe. The conical shape of a silicone plug described herein allows for a more efficient collection of, for example, nucleated cells (including stem cells from bone marrow, e.g., mesenchymal stem cells (MSCs) or hematopoietic stem cells (HPCs)). The device reduces opportunity for contamination by decreasing the number of transfers required to prepare a sample, as the sample does not need to be transferred to a secondary device for centrifugation. A biological fluid such as bone marrow aspirate or whole blood can be isolated from a patient and centrifuged in the same device. Furthermore, the device holds a substantial volume (e.g., about 20, 30, 40, 50, 60, 70, 80, or 100 mL, or more) of extracted biological fluid, eliminating the need to switch out syringes during withdrawal.

Methods are described herein that produce a therapeutic fluid with a high concentration of growth factors, cytokines, and proteins, in a simplified and fast manner. In some embodiments, the therapeutic fluid is autologous conditioned bone marrow concentrate (ACBMC) or platelet rich plasma (PRP). A syringe device can provide compositions (i.e., therapeutic fluids) with, for example, increased anabolic and anti-inflammatory cytokines for treatment of human or non-human (e.g., canine, equine, bovine, etc.) damaged tissue such as cartilage, bone, tendon, muscle, ligament, and neurological tissue.

In an embodiment, a locking support cage interacts with a locking support clip to prevent regression of a syringe plunger as it is retracted. A locking support cage has one or more ridges, and the locking clip has one or more protrusions on its inner surface. The one or more ridges and the one or more protrusions interact to prevent the support cage (and a syringe plunger) from regressing after retraction.

In an embodiment, a device comprises a double syringe, for example an outer syringe body (first syringe) and an inner syringe body (a second syringe) located at least partially within the outer syringe body, or a first syringe in direct fluid communication with a second syringe. A locking cage surrounds the second syringe, and a locking clip fastens or locks around the finger grips of the first syringe. As a plunger in the second syringe is withdrawn, the interaction between the one or more ridges and the locking cage allow the plunger to retract, but not to regress (that is, not move back into the syringe). This mechanism allows for more efficient removal of bone marrow aspirate or other biological fluids.

In an embodiment, a biological fluid such as bone marrow aspirate or whole blood is obtained from a patient and stored in the outer syringe body. To extract a biological fluid, a needle is attached to the device and inserted into a patient. The syringe plunger is retracted and controlled by a locking cage and locking clip to collect a biological fluid. The obtained aspirate is then separated, for example by centrifugation, to retrieve therapeutic fluids, such as platelet rich plasma and/or bone marrow cell concentrate. At least part of the therepeutic fluid (e.g. platelet rich plasma or bone marrow cell concentrate) is drawn into the inner (or second) syringe. The therepeutic fluid can be subsequently employed in surgical repairs, promoting the healing of the repair and promoting tissue growth in orthopedic and neurological applications, for example.

Locking Support Cage

Embodiments of a device comprising a locking support cage are exemplified herein at, inter alia, FIGS. 1-4. A locking support cage comprises a tubular body with an aperture running the entirety of its length, almost the entirety of its length, at least 90% of its length, at least 85% of its length, at least 80% its length, at least 75% of its length, at least 60% of its length, or a majority of its length. A locking support cage can have at least one ridge disposed on its outer surface. The aperture running lengthwise can accommodate the body of a syringe. The locking cage is configured to interact with a locking clip (described below), and in some embodiments, a gasket (described below). The aperture of the locking cage is configured to surround the body of a syringe (see e.g., FIG. 1, 2). The at least one ridge allows a locking clip to catch on the locking cage during use of the device.

The locking cage comprises at least one ridge (e.g., about 1, 2, 3, 4, 5, 10, 15, 20, or more ridges) on its outer surface. The outer surface of the locking cage can have multiple ridges (see e.g., FIG. 4). In some embodiments, the at least one ridge forms an oblique angle relative to the body of the cage (see e.g., FIGS. 4, 5).

Figure 3:
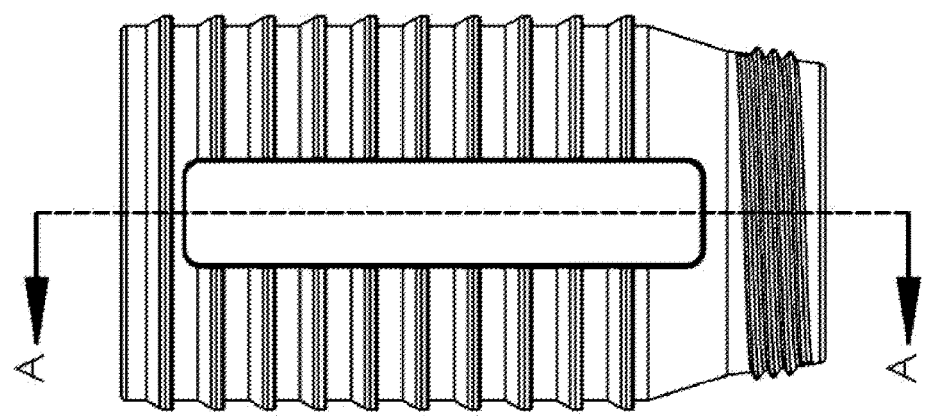
FIG. 3 illustrates a side view of a locking cage of a device for controlling the movement of a syringe plunger. Viewing windows are shown, and Section A-A is designated.

The locking cage can optionally be reattached to the syringe after centrifugation for added stability. The locking cage can have viewing windows allowing for easier isolation of certain fluid fractions (e.g., a buffy coat fraction) post-centrifugation (FIGS. 1, 3). These windows can minimize "unwanted" cells and isolate "wanted" cells (e.g., bone marrow-based stem cells) by giving the user the ability to view the cells as they are funneled up into the device. This allows for more selectivity as to what material is pulled into the second or inner syringe.

The locking support cage can have one terminus that is narrower than the other terminus. The narrower terminus can be threaded (see e.g., FIG. 3, 4). The locking support cage can be made of polypropylene or another solid, nonabsorbent material, and can be at least partially translucent. The locking cage can be reusable, i.e., it can be used in the collection of multiple samples.

Swabbable Valve, Gasket, and Plug

In some embodiments, a device comprises one or more of a swabbable valve, gasket, and plug. One or more of these three elements can interact with one or more of the other elements.

In some embodiments, a device comprises a swabbable valve 200. Swabbable valves comprise a valve body and a stem. A variety of swabbable valve configurations are known in the art and can be used in the device. These include, but are not limited to, straight male threaded swabbable valves, straight female swabbable vales, and tube end swabbable valves. Any type of valve or connector can be used including, for example, an open luer lock with a separate cap to close the opening. In some embodiments, the swabbable valve body is made of polycarbonate or polyvinyl chloride (PVC). In some embodiments, the swabbable valve comprises a stem made of silicone.

Figure 4:
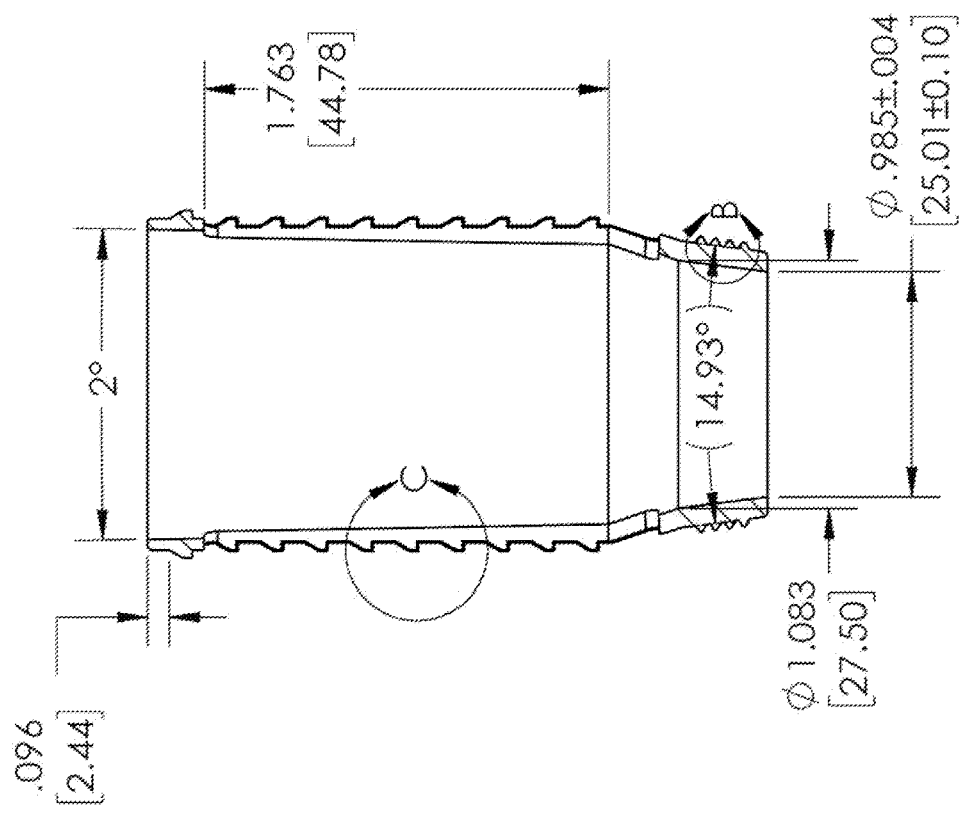
FIG. 4 illustrates a side view of Section A-A of a locking cage of a device for controlling the movement of a syringe plunger. Detail B and C areas are designated.
Figure 5:
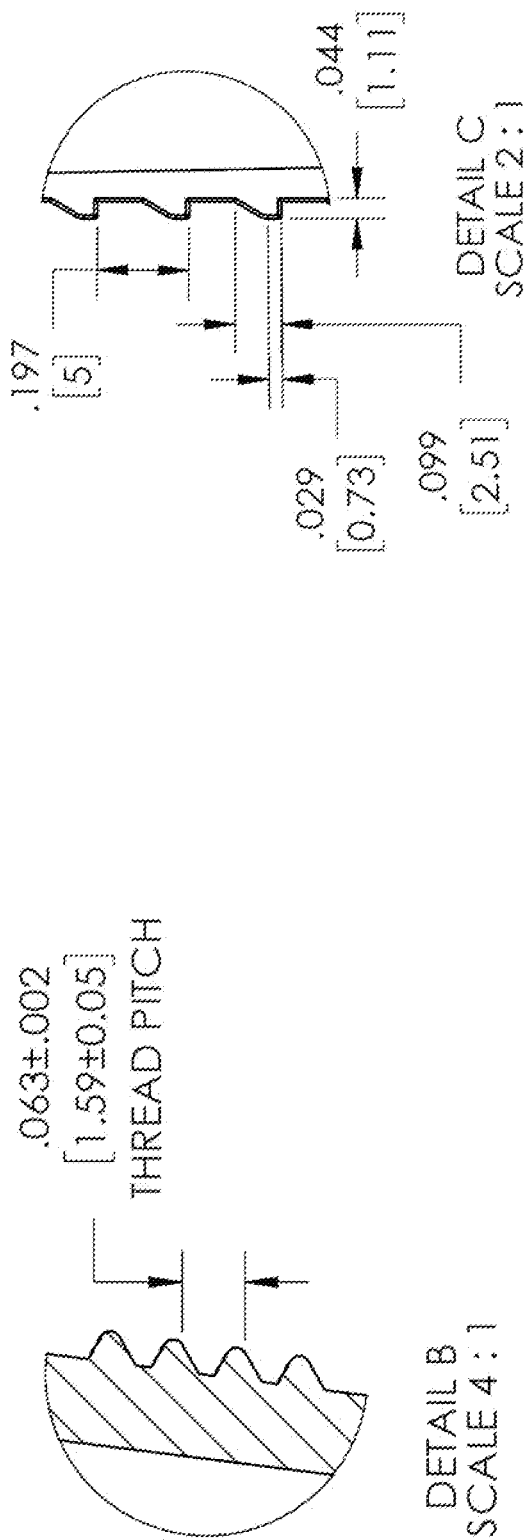
FIG. 5 illustrates side views of Detail B (top) and Detail C (bottom) areas of a locking cage of a device for controlling movement of a syringe plunger. Detail B shows the threading on the locking cage (for attachment to a gasket). Detail C shows the ridges.
Figure 6:
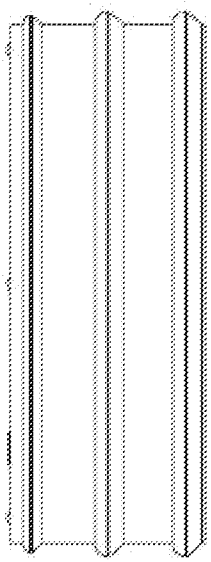
FIG. 6 illustrates perspective (top) and side (bottom) views of a swabbable valve, a gasket, and a silicone plug of a device for controlling the movement of a syringe plunger. The perspective view shows the pieces interacting, while the side view shows them separated.
Figure 6:
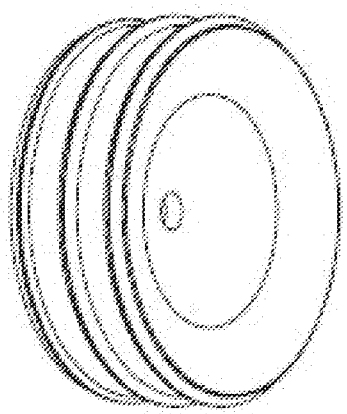
Figure 6:
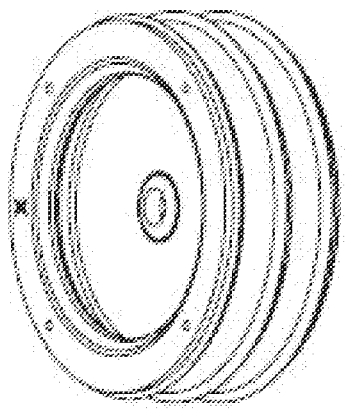
Figure 7:
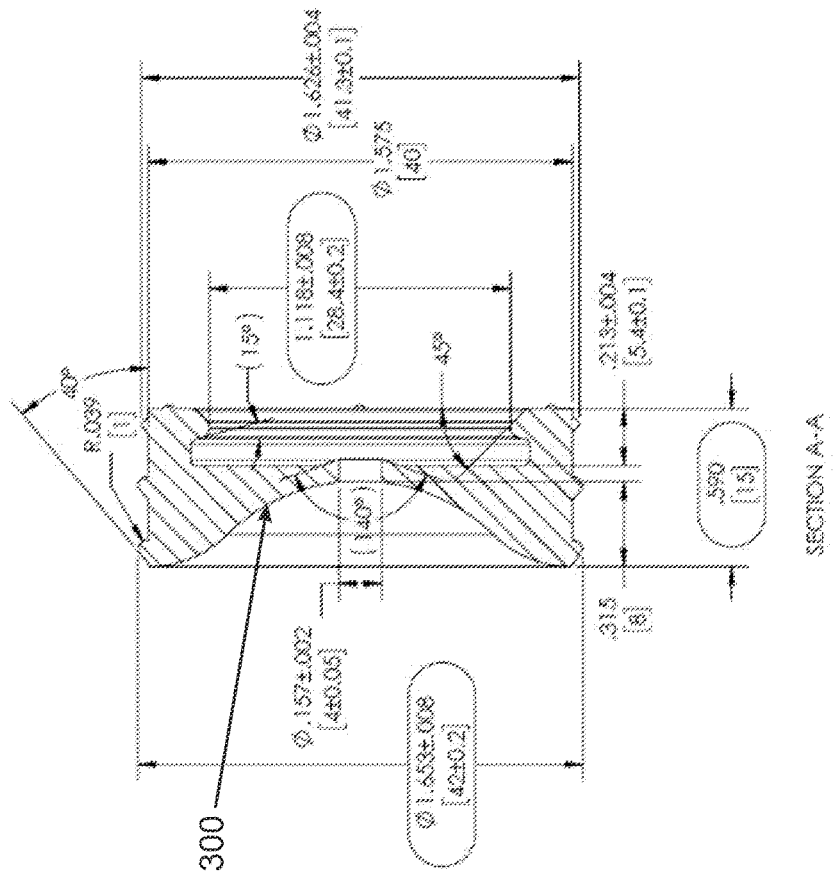
FIG. 7 illustrates side (top) and cross-section (bottom) views of a swabbable valve, a gasket, and a silicone plug of a device for controlling the movement of a syringe plunger. The three pieces are shown interacting in both views. The cross-section view shows threading to allow the gasket to interact with the locking cage, as well as the fit mechanism allowing the interaction between the gasket and the silicone plug. The gasket and the silicone plug can have coordinating geometries so that the protrusion on the gasket fits into a cut out on the silicone plug. This interaction can prevent the two parts from easily disassembling.
Figure 7:
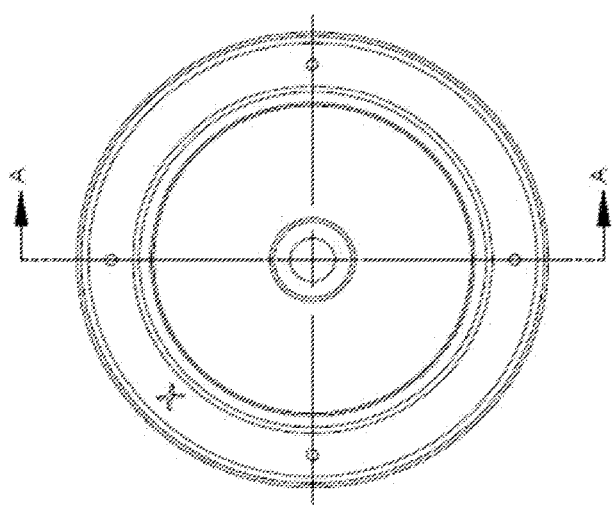

In some embodiments, a device comprises a gasket (see e.g. FIGS. 6, 7). In some embodiments, the gasket comprises an outer surface made of silicone or another soft, flexible material. In some embodiments, the locking support cage of the device can interact with the gasket through a threading mechanism. FIGS. 3 and 4 show threads on the locking support cage, and FIG. 7 shows threading on the gasket with which the threading on the locking cage can interact.

In some embodiments, a device comprises a plug 100 made of a soft, flexible material (e.g., silicone) (see e.g. FIGS. 6, 7). The plug has an aperture to allow passthrough of material (see e.g. FIGS. 6, 7). The plug can be made out of translucent material to allow for visibility and thus more selectivity of material passing through the aperture. The plug (e.g., a silicone plug) can have at least one concave (versus convex or flat) surface 300 oriented toward the distal end of the device, opposite the locking cage, to allow for more efficient collection of cells from a biological fluid (e.g. MSCs and HPCs from bone marrow) (see e.g., FIGS. 6, 7).

In some embodiments, the concave surface on the plug has a conical recess (see e.g., FIG. 7). The plug can be made of silicone or another suitable soft, flexible material.

Figure 8:
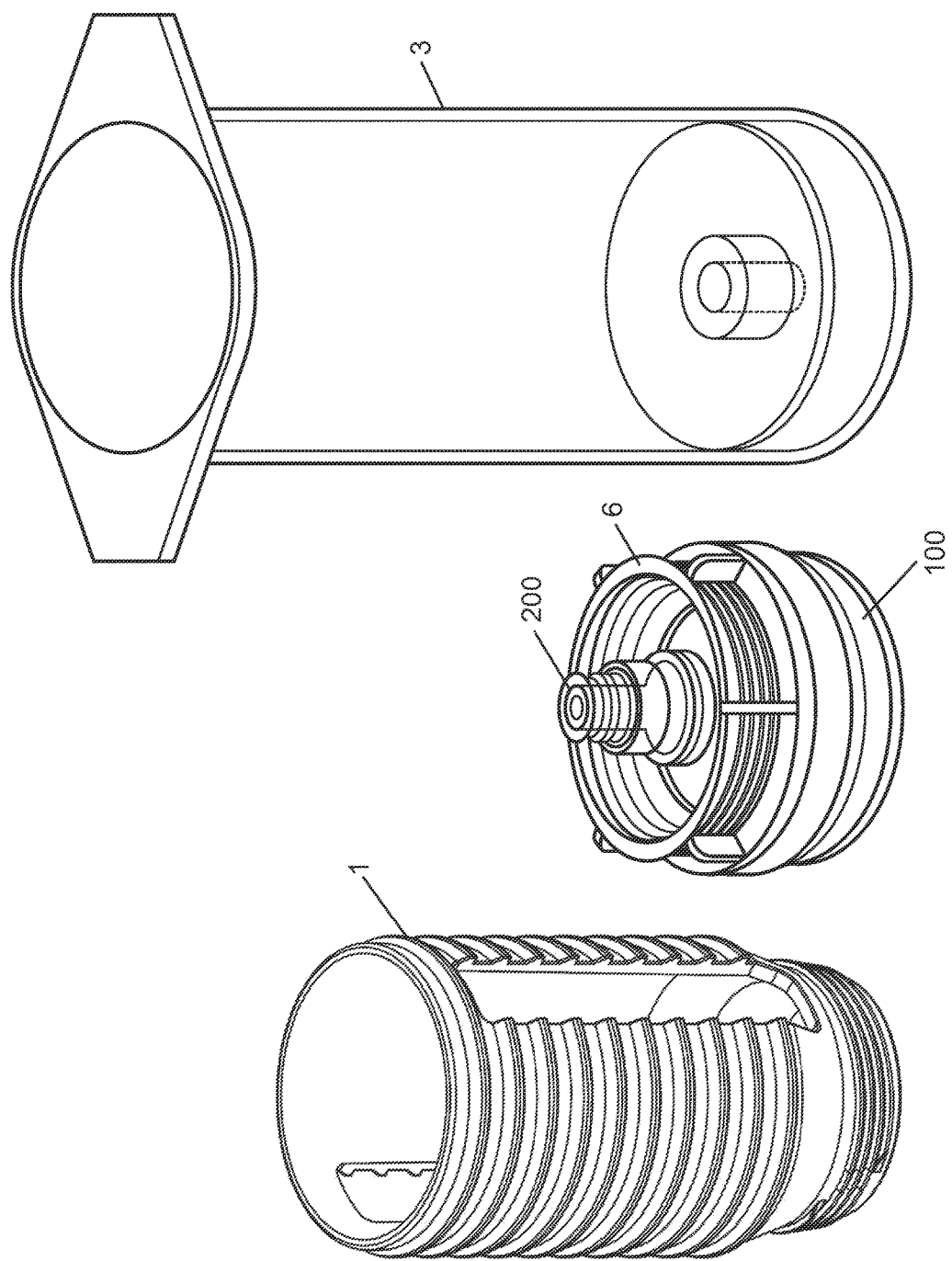
FIG. 8 is a photograph of (from left to right) a locking cage, a swabbable valve/gasket/silicone plug piece, and a first syringe of a device for controlling the movement of a syringe plunger.
Figure 9:
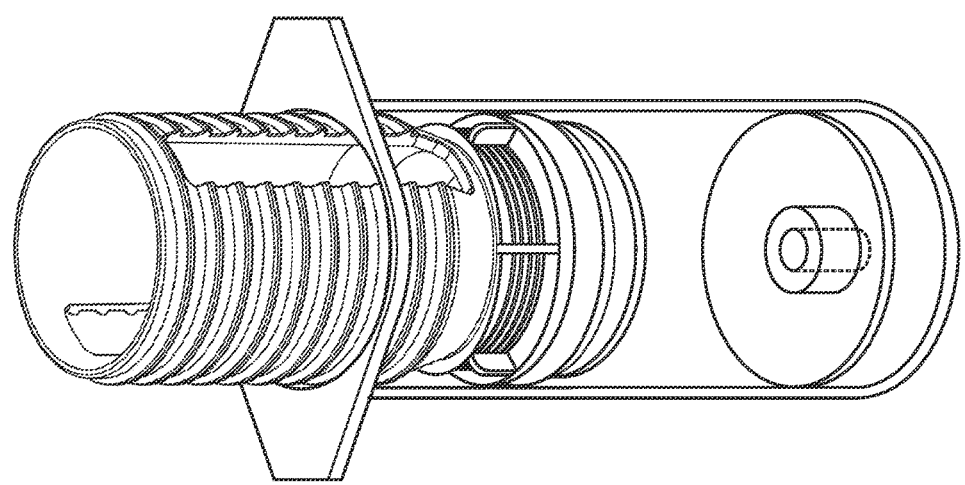
FIG. 9 is a photograph of a locking cage interacting with a gasket. Both pieces are nested within a first syringe of a device for controlling the movement of a syringe plunger. A swabbable valve and silicone plug are also shown.

FIGS. 8-9 show separately and together the components of part of a device of the present disclosure. FIG. 8 shows the parts of a locking cage, swabbable valve/gasket/plug, and first syringe. FIG. 9 shows a locking cage threaded into a gasket (with swabbable valve and plug) and inserted into a first syringe.

Locking Clip

A device can further comprise a locking clip (see e.g., FIGS. 10-13). The locking clip can be configured to surround a locking cage and includes an inner surface configured to interact with the ridge or ridges of the locking cage.

The locking clip functions to prevent a plunger of a syringe that is positioned within the aperture of the locking cage from regressing after it is retracted.

Figure 10:
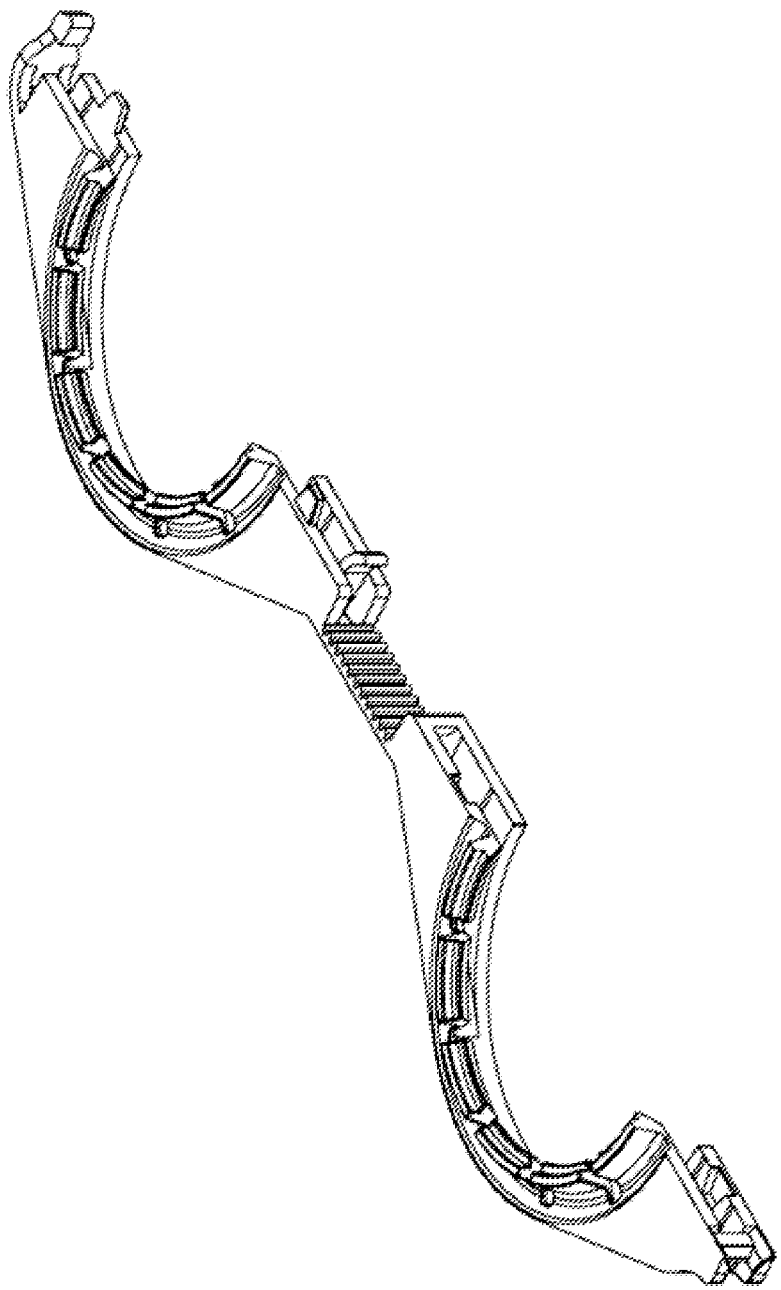
FIG. 10 illustrates a perspective view of a locking clip of a device for controlling the movement of a syringe plunger.
Figure 11:
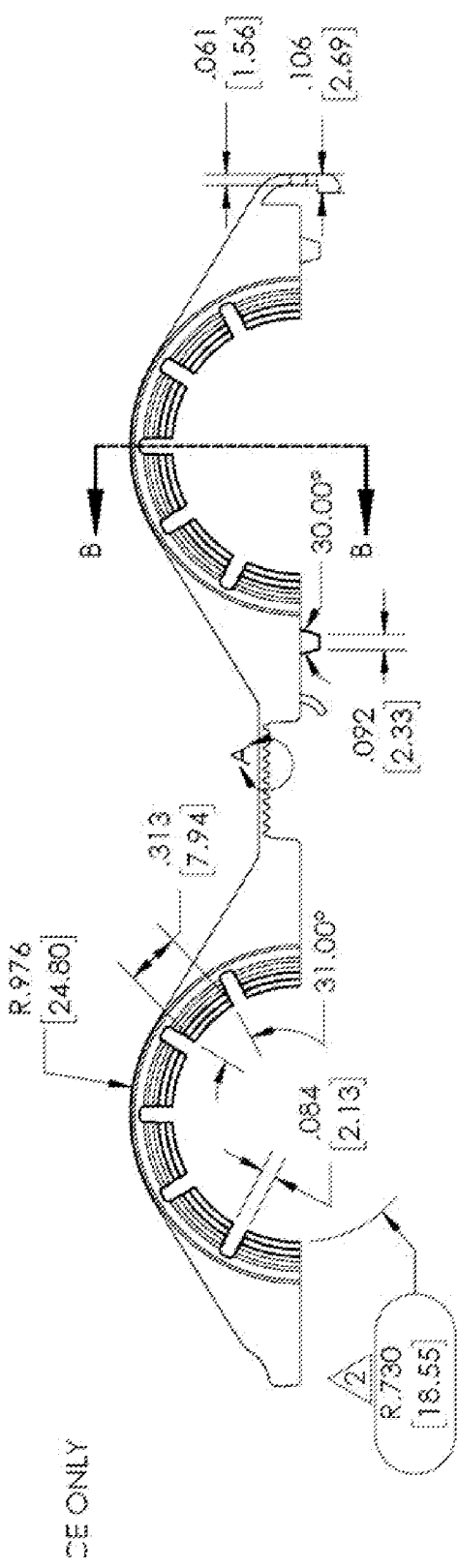
FIG. 11 illustrates a top view of a locking clip of a device for controlling the movement of a syringe plunger. Detail A and Section B-B are designated.
Figure 12:
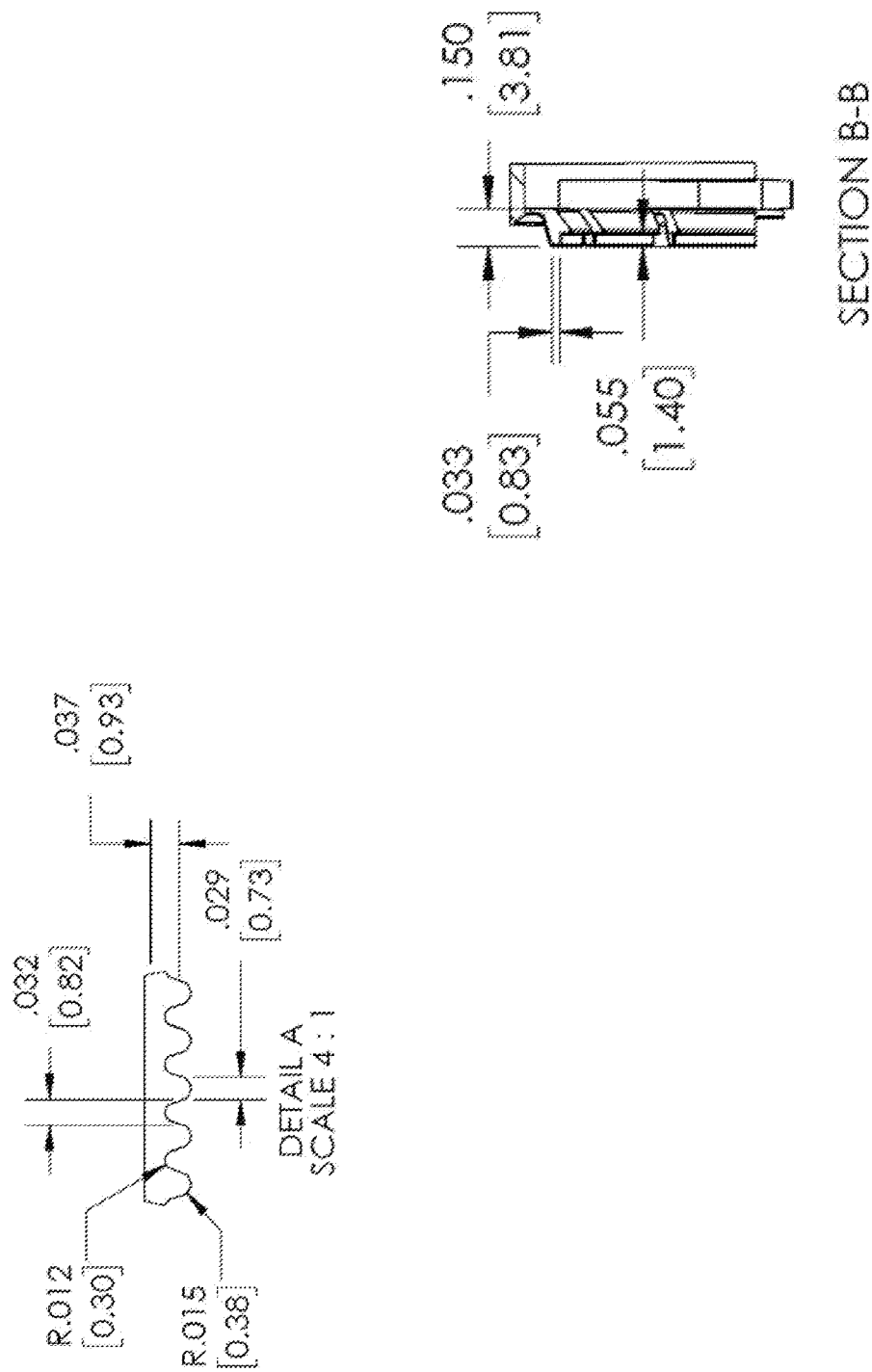
FIG. 12 illustrates a top view of Detail A (hinge, top) and Section B-B (bottom) of a side view of a locking clip of a device for controlling the movement of a syringe plunger.
Figure 13:
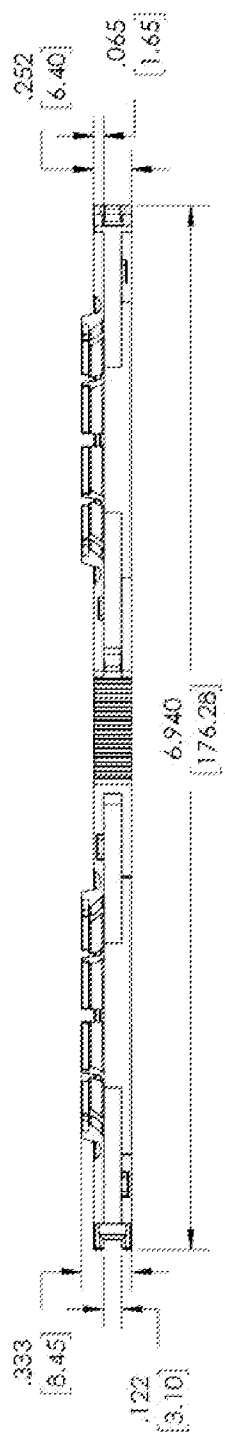
FIG. 13 illustrates a side view of a locking clip of a device for controlling the movement of a syringe plunger.

In some embodiments, the locking clip is hinged (see e.g., FIGS. 10, 11). In some embodiments, the locking clip has one or more protrusions configured to catch on the ridge or ridges of a locking cage (see e.g., FIGS. 10-12). The locking clip can be made of polypropylene or another solid, nonabsorbent material.

Figure 14:
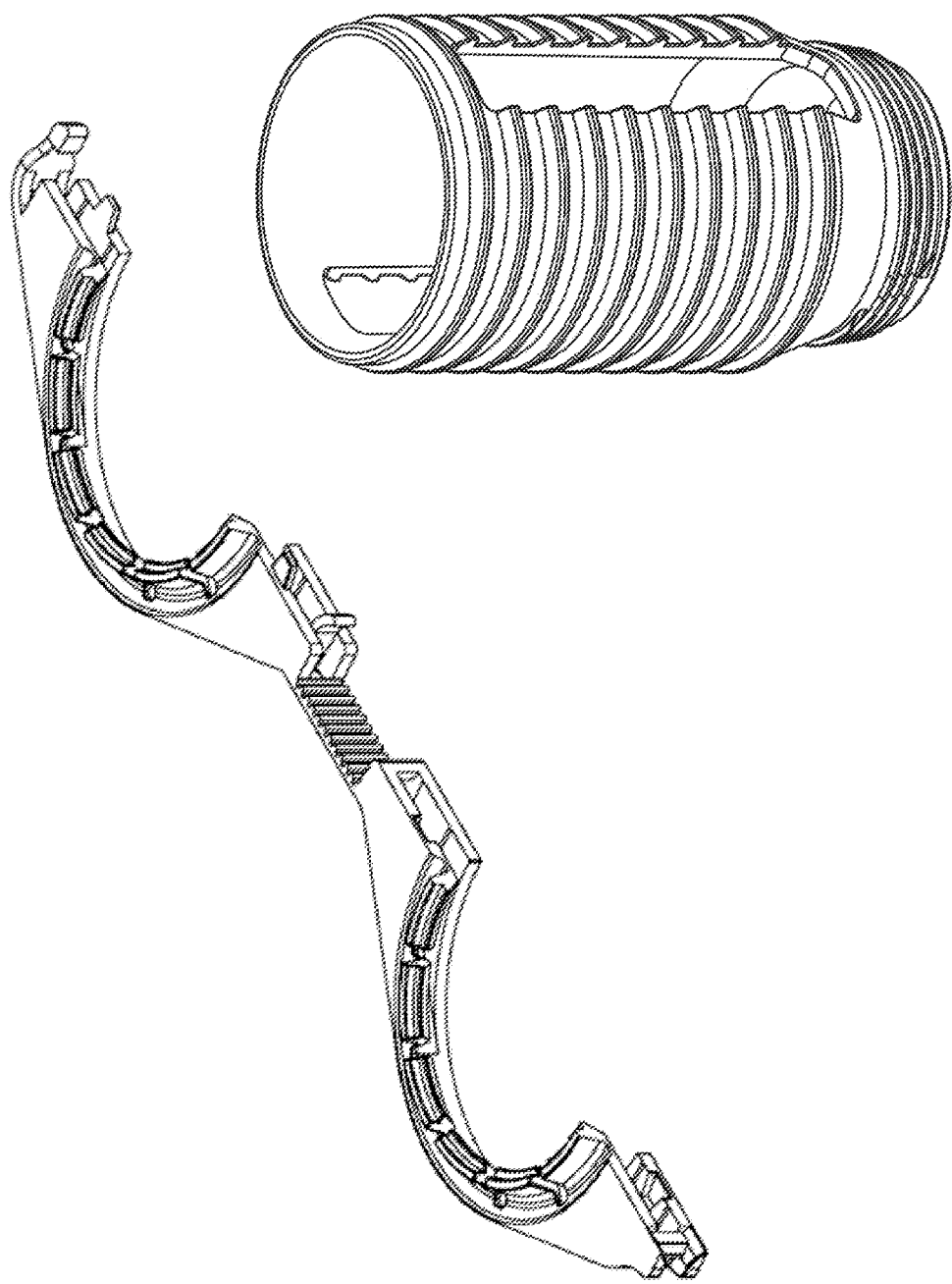
FIG. 14 is a photograph of a device for controlling the movement of a syringe plunger. A locking clip (2, left) and a locking cage (1, right) are shown. The locking cage and locking clip are shown separately.
Figure 15:
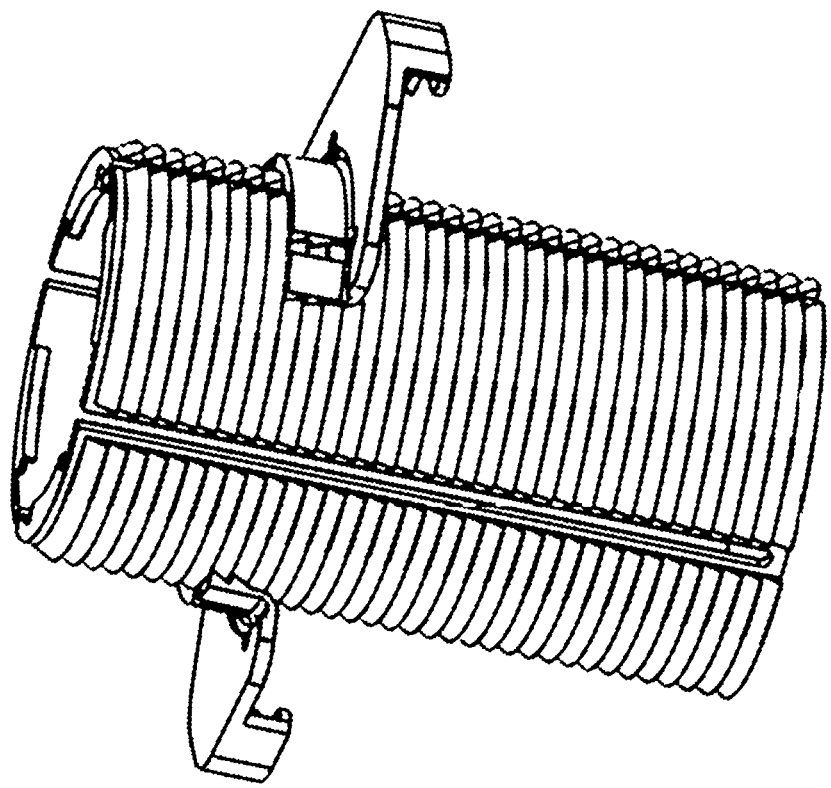
FIG. 15 illustrates a perspective view of a device for controlling the movement of a syringe plunger. A locking cage (1) and a locking clip (2) are shown. The locking cage and locking clip are shown interacting.
Figure 16:
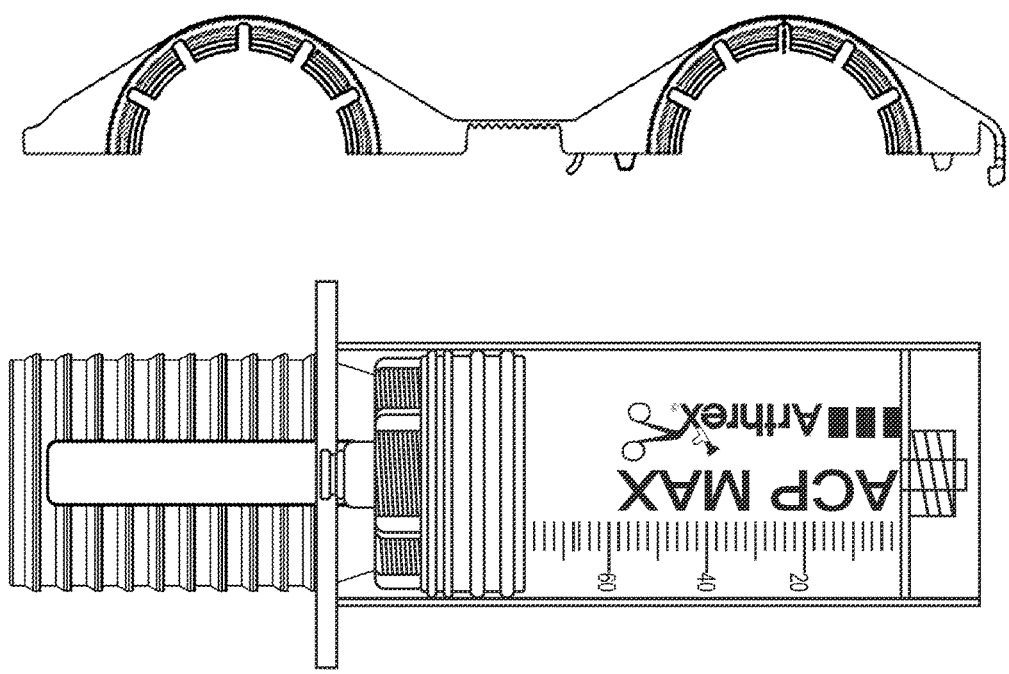
FIG. 16 is a photograph of a locking cage interacting with a first syringe (left), as well as a locking clip (right) of a device for controlling the movement of a syringe plunger. The locking clip is shown separate from the locking cage.
Figure 17:
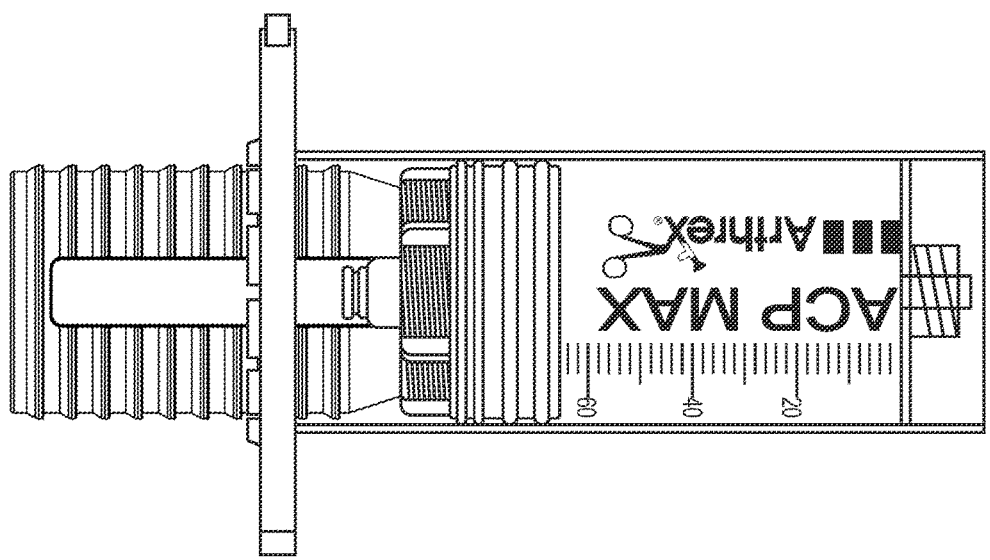
FIG. 17 is a side view photograph of a locking cage and locking clip (dark) interacting with a first syringe (white) of a device for controlling the movement of a syringe plunger. A gasket can be seen within the syringe, interacting with the locking cage. A swabbable valve and silicone plug are also present.

The locking clip can be attached and removed as needed (FIG. 14 shows the locking clip (2), removed from the locking cage (1)). The locking clip is configured to fit around a locking cage to control the movement of a syringe plunger, catch on the ridges of the support cage, and lock into place (FIG. 15, with locking cage shown as 1 and locking clip shown as 2). The locking clip can be configured to fasten around the finger grips (wings or collar) of a first or outer syringe body (FIGS. 16-17).

Syringes

A device as described herein can include two or more syringes. A syringe is a device used to inject or withdraw biological fluids or tissues from a subject. Many syringe designs are known in the art. In general, the device has a hollow cylindrical body made of a hard material, such as glass or plastic. The cylindrical body can have finger grips (wings or collar) protruding from the outside of the tubular body to allow the device to be more easily held. The finger grips can be positioned at the proximal end of the cylindrical body. A piston or plunger can be present in the cylindrical body of the syringe. The piston or plunger can fit tightly within the cylinder and can have a terminus or flange that blocks one terminal opening of the hollow cylindrical body. The syringe can be fitted with a needle (e.g., for insertion into a subject) at the distal end, but can also terminate in a nozzle, tubing, or other configuration.

Devices can comprise "nested" syringes. Nested syringes comprise one or more smaller syringes positioned within the cylindrical body of a larger syringe from which the plunger has been removed. In a set of nested syringes, only the innermost syringe has a plunger. The cylindrical body of an inner syringe can act as a plunger for an outer syringe, particularly if the cylindrical body is connected to a gasket. In some embodiments of the present disclosure, two syringes are nested. In some embodiments, three syringes are nested. Other tubular bodies, such as a locking support cage, can be nested between the syringes.

In other embodiments, a device can comprise a series of syringes. Syringes in series comprise multiple syringes in which each syringe is in fluid communication with at least one other syringe in the device. Each syringe in the series can be of absolute or relative size. In a series of syringes, each syringe can have a plunger.

Plungers

Devices can include syringe plungers. A syringe plunger is a device used to move material within the cylindrical body of a syringe. Syringe plunger designs are known in the art. In general, the device is a shaft made of, for example, hard plastic material with a flange at one terminus and a seal at the other terminus. The flange is made of hard material intended to bear pressure (for example, pressure exerted by a user's thumb). The seal is configured to form a liquid seal between the plunger and the cylindrical body of the plunger, and can be made of a pliable material. The seal moves linearly up and down the cylindrical body of the syringe in response to pressure applied at the flange. A vacuum can form within the cylindrical body of the syringe in response to the seal moving from the distal terminus to the proximal terminus of the cylindrical body. In some embodiments, the cylindrical body of a nested syringe can act as a syringe plunger. Any of the syringe bodies of the present disclosure can be construed as a plunger in the embodiments described. In some embodiments, the cylindrical body of the nested syringe acting as a plunger is connected to a gasket.

These devices can control the linear movement of a plunger. When withdrawing body fluid or tissue from a subject, it is often desirable that a vacuum be maintained in order to keep material moving from the subject into the body of a syringe. To maintain a vacuum within the body of a syringe, the seal should not be allowed to retract in response to the building pressure as it is moved from the distal to the proximal end of the syringe. Therefore, these devices provide a locking mechanism to prevent regression of a syringe plunger as it is retracted.

Devices

Figure 18:
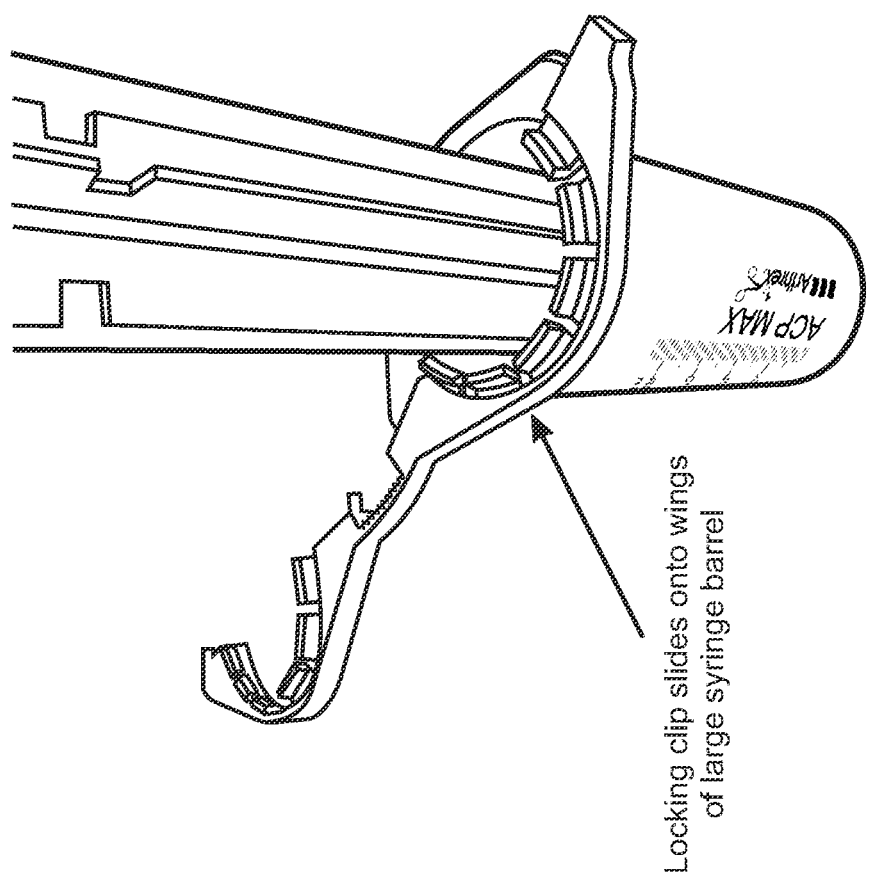
FIG. 18 is a perspective photograph of a device for controlling the movement of a syringe plunger. A first syringe, second syringe with plunger, and locking clip can be seen. The locking clip is shown in the open position.
Figure 19:
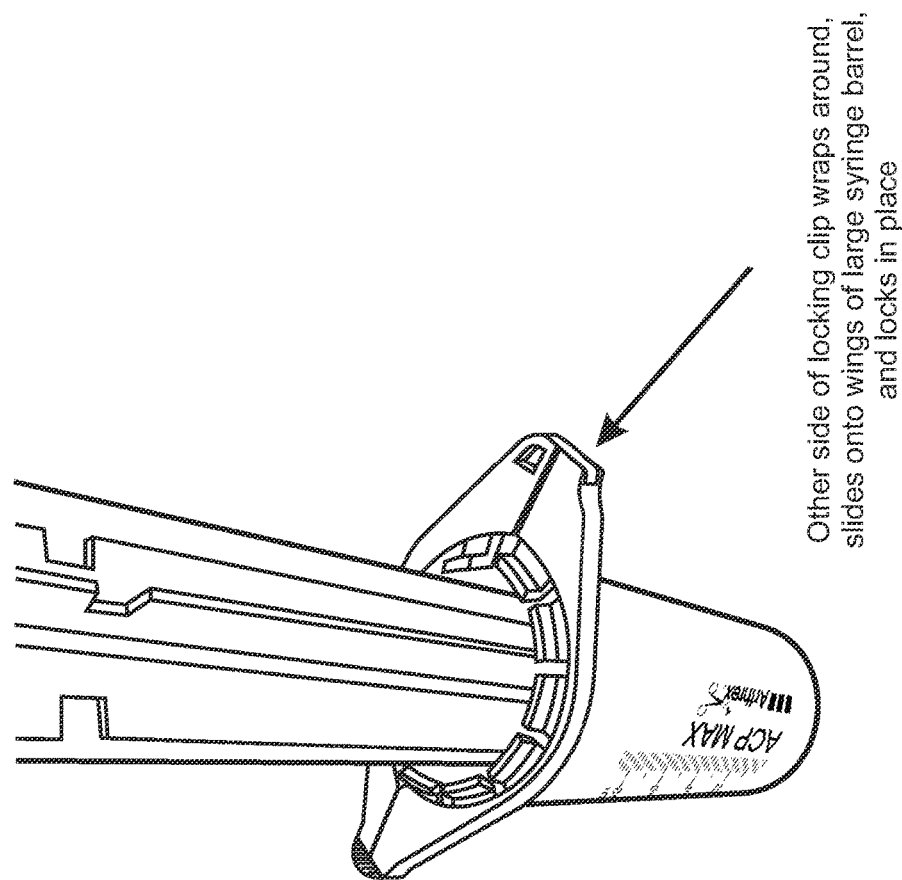
FIG. 19 is a perspective photograph of a device for controlling the movement of a syringe plunger. A first syringe, second syringe with plunger, and locking clip can be seen. The locking clip is shown in the fastened or locked position.

A device can include two or three syringe bodies, a plunger, a locking support cage, and a locking clip. Optionally, a swabbable valve, gasket, and/or plug is included in the device. FIGS. 18 and 19 show perspective photographs of the device with a locking clip open and closed.

Figure 20:
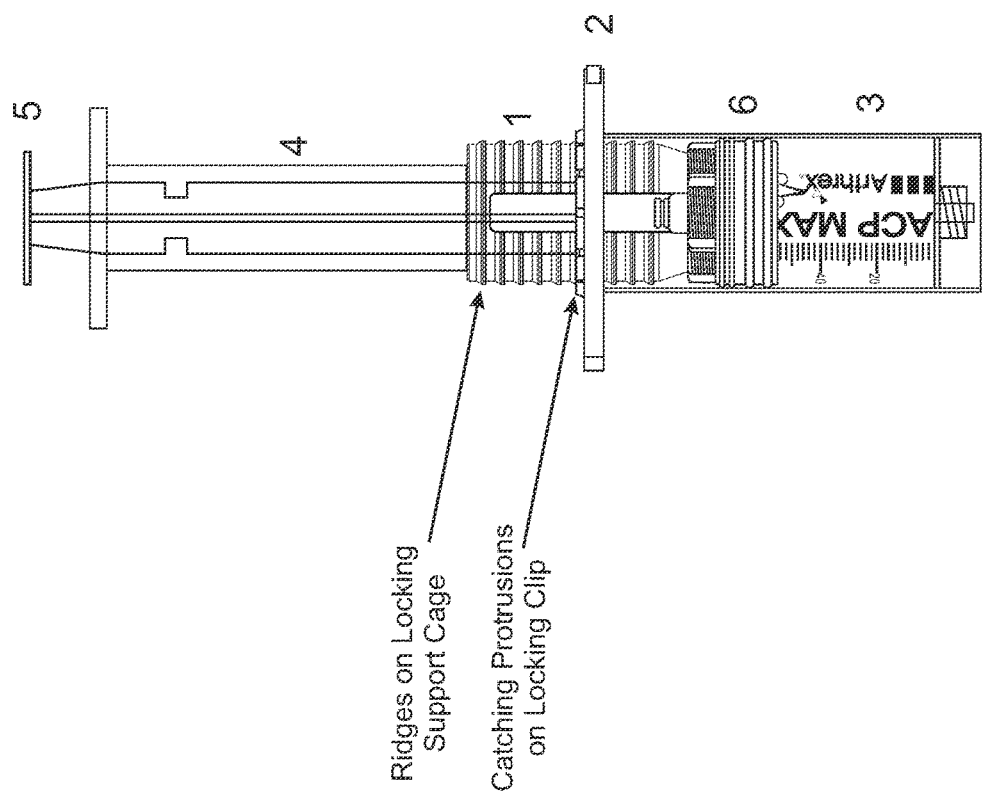
FIG. 20 is a side view photograph of a device for controlling the movement of a syringe plunger. A locking cage (1), locking clip (2), first syringe body (3), second syringe body (4), second syringe plunger (5), and gasket (6) are shown.

One embodiment of a device shown in FIG. 20. A device can be fitted with a needle that can be inserted into a subject to withdraw biological fluid or tissue. In this device, as the second syringe body (acting as a plunger) 4 is retracted linearly through the body of the first syringe 3, the ridges on the locking support cage 1 glide past the protrusions on the locking clip 2. Due to the presence and/or shape of the ridges, the plunger can be pulled out (retracted) but not pushed back in (regressed). Once a ridge on the support cage passes the protrusion on the locking clip, it cannot go back easily. This allows for pulling the plunger of the device to create a vacuum and the ridges/protrusions to hold the vacuum and prevent the plunger from going back into the device. The vacuum can draw body fluid or tissue such as bone marrow aspirate into the body of the first syringe 3.

Figure 21:
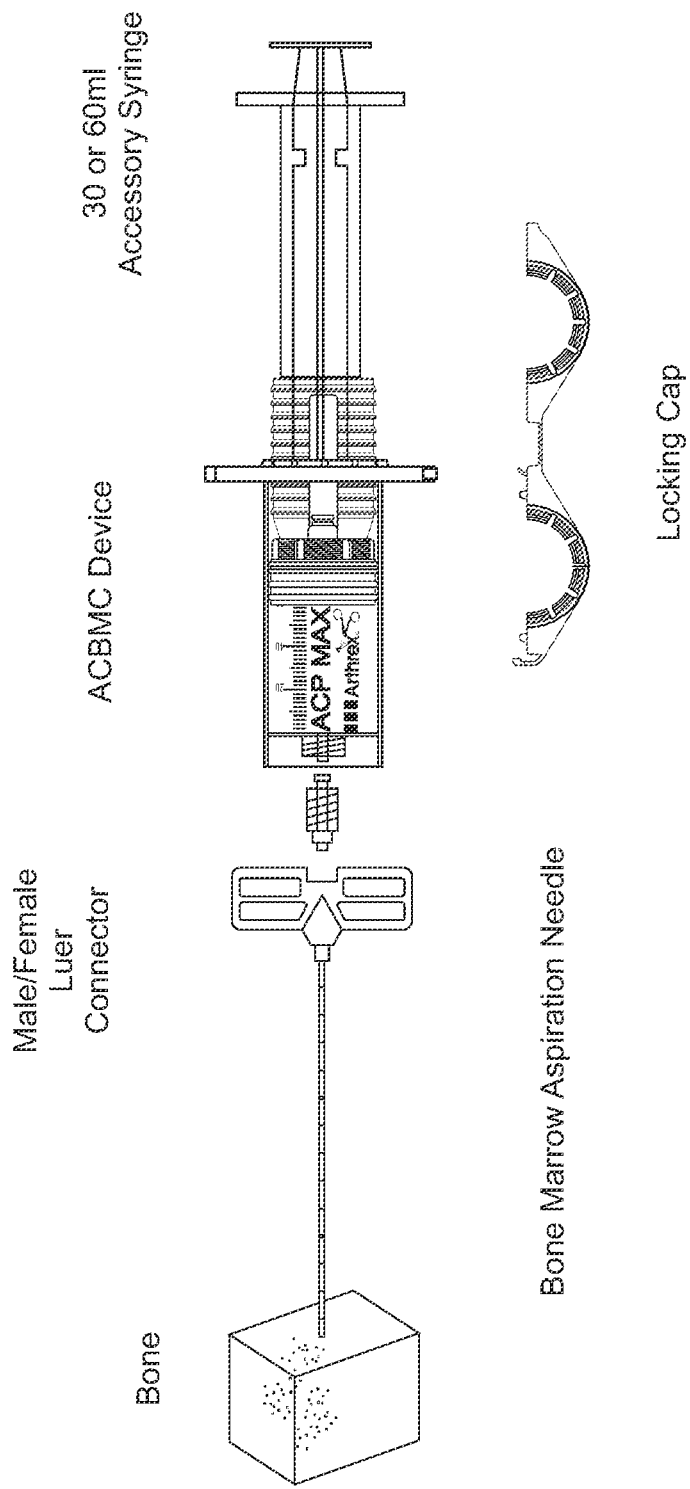
FIG. 21 is a side view photograph of a device for controlling the movement of a syringe plunger along with a Luer connector, bone marrow aspiration needle, and bone model. A locking cage, locking clip, first syringe body, second syringe body, and second syringe plunger are shown. The locking clip is shown separate from the rest of the device.
Figure 22:
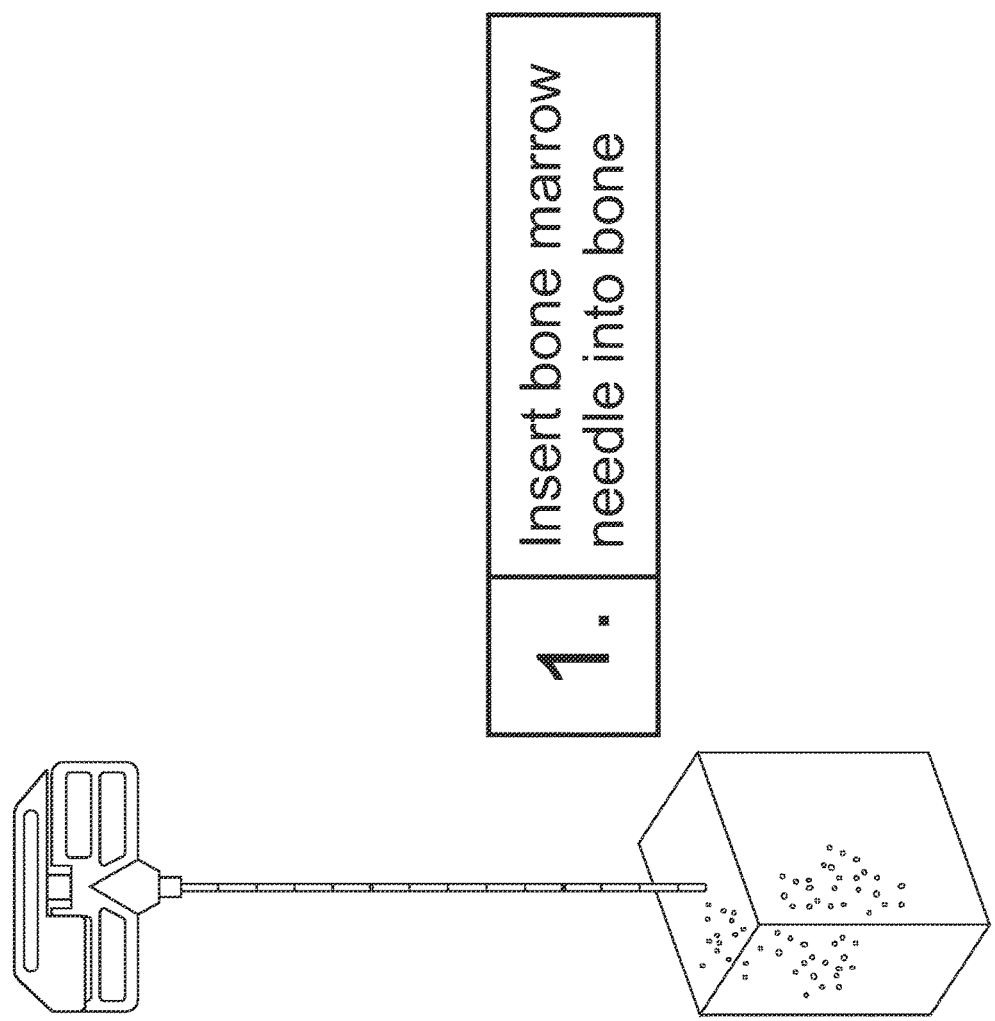
FIGS. 22-28 are photographs of depicting a method of obtaining a therapeutic fluid using a device for controlled positioning of a syringe plunger. Steps 1-7 are shown, with the components of the device shown as positioned in each step.
Figure 23:
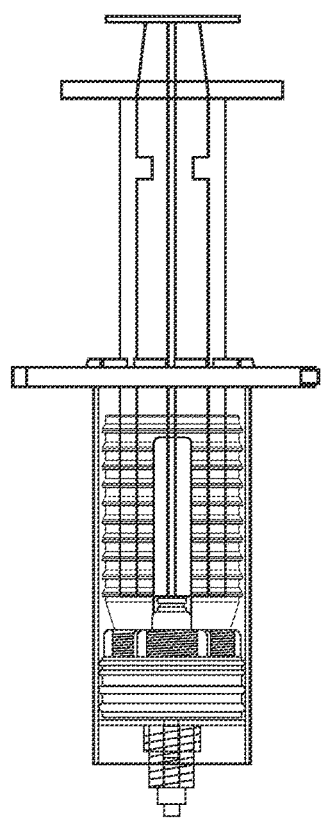
Figure 24:
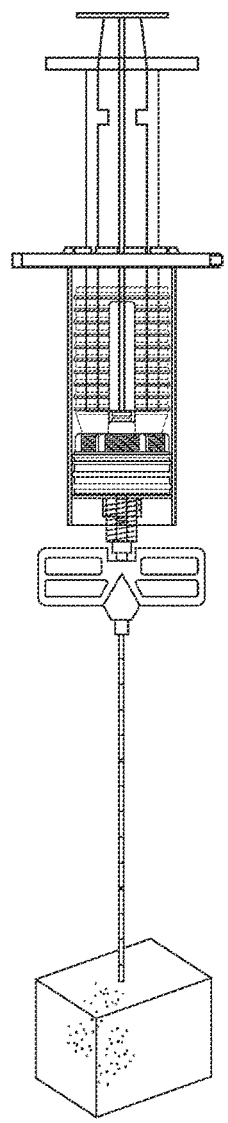
Figure 25:
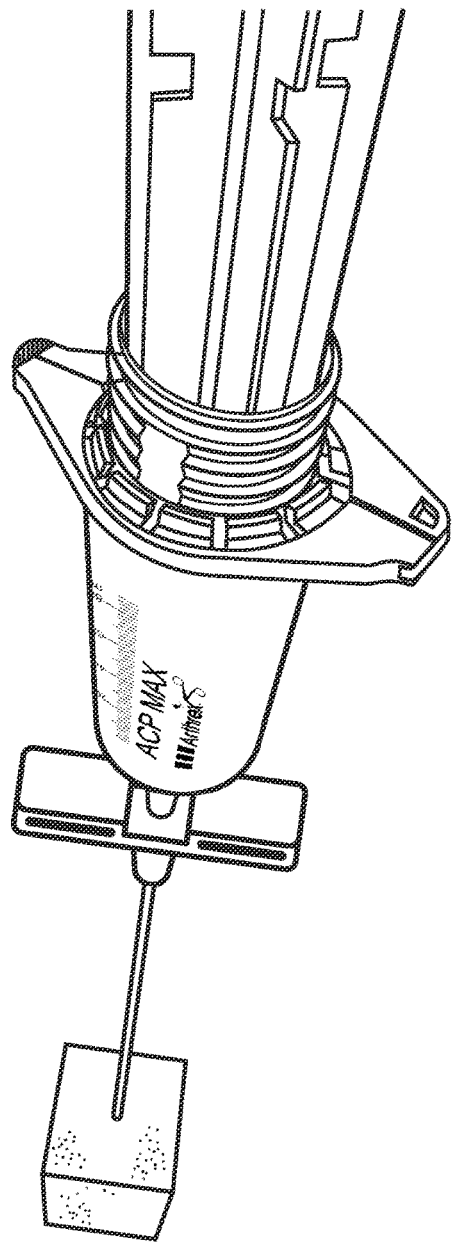
Figure 26:
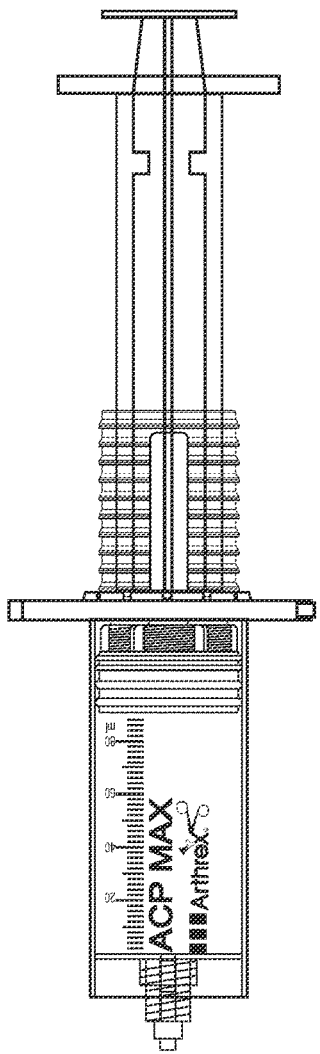
Figure 27:
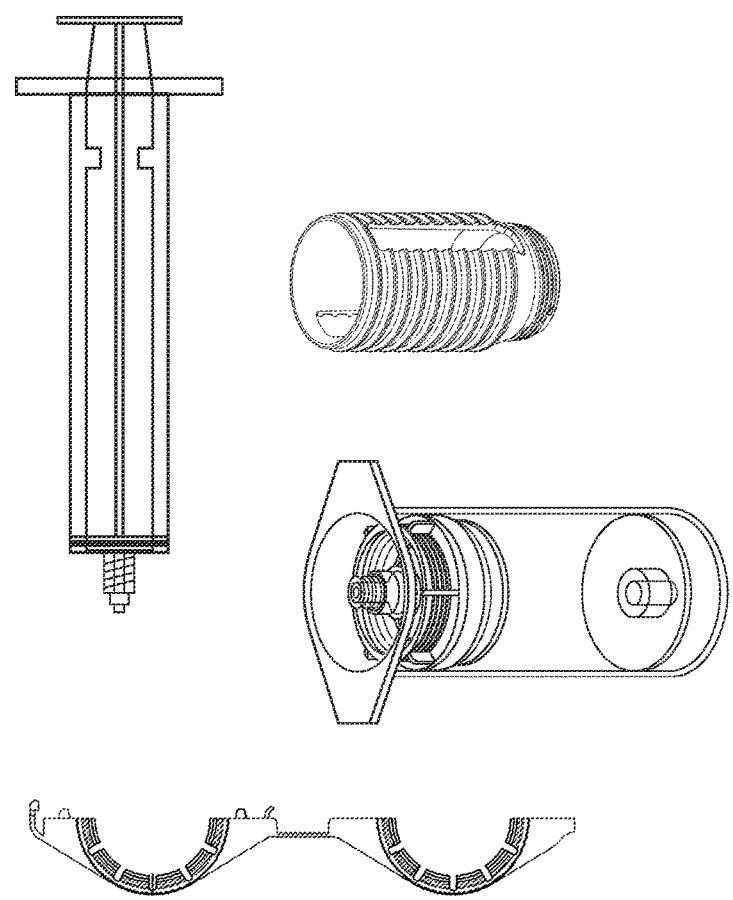
Figure 28:
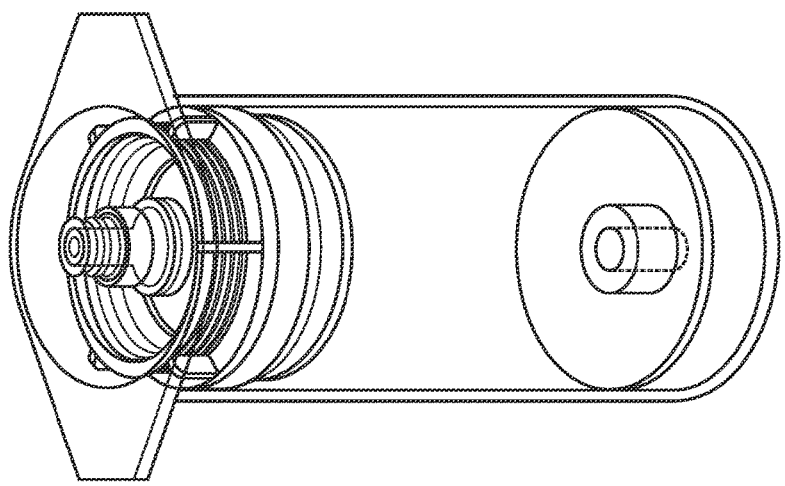
Figure 29:
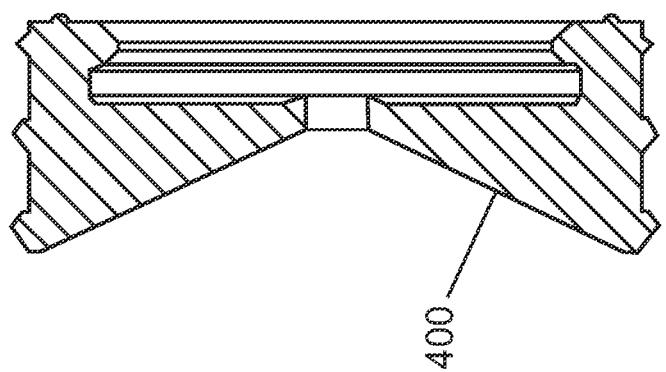
FIG. 29 shows a plug.

In some embodiments, the locking cage is fitted into a gasket. The gasket interacts with a plug comprising an aperture and a concave surface positioned opposite the locking cage 6. After the sample is drawn into the body of the first syringe 3 and subsequently centrifuged, the flow of material into the second syringe body is controlled by a concave surface and the aperture. The concave shape of the plug thus allows for a more efficient collection of, for example, nucleated cell concentration (including stem cells from bone marrow, e.g., MSCs, HPCs, etc.). In some embodiments, the concave surface has a conical shape 400. In some embodiments, the device comprises three nesting syringes of different diameters. FIG. 21 shows a device with locking clip separately, as well as some additional components that can be used in conjunction with the device: a bone marrow aspiration needle and a Luer connector.

Methods of Producing Therapeutic Fluid

Biological fluids, such as bone marrow or whole blood, can be harvested as shown in FIGS. 25-31. Using a two-syringe device, a butterfly-cannula (or other suitable cannula or needle) can be attached to a hole of the double syringe. The cannula or needle can be attached via a Luer lock to create a locked seal. A double syringe can be used to aspirate the biological fluid by moving the inner syringe body (acting as the plunger) away from the distal end of the first syringe body that is attached to the cannula or needle. The locking cage and locking clip features can be used as needed to draw out the aspirate. An anticoagulant, for example, heparin, sodium citrate, citrate, or phosphate dextrose, can be added to the biological fluid (e.g., bone marrow or whole blood) to keep it from clotting. The butterfly-cannula can then replaced by a Luer lock cap or plug, the locking cage and locking clip can be removed, and the first syringe, still connected to the gasket, can be centrifuged to separate the biological fluid (e.g., bone marrow or whole blood) into fractions such as platelet rich plasma, plasma, buffy coat, leukocyte-reduced PRP, and/or red blood cells. In one embodiment, the fractions are platelet poor plasma (top), buffy coat (middle), and erythrocyte (bottom). In another embodiment the fractions are plasma (e.g., platelet rich plasma) (top layer) and eyrthorcyte layer (bottom).

A device can be be spun at a speed suitable to produce the desired end product. This will vary based on the fluid type, starting volume, and desired end product (type of cells and volume). Any suitable centrifuge speed and time can be used. In an embodiment, a biological fluid or tissue such as whole blood, bone marrow, or a combination thereof, can be centrifuged at a relative centrifugal force (RCF) that is equal to or less than 2665×g but still fractionates the fluid or tissue into a plasma layer, a buffy coat layer, and an erythrocyte layer (e.g., a hard spin). In some embodiments, a sample is centrifuged with a "hard spin" at 1700×g. In an embodiment, a sample can be centrifuged at about 1500×g, about 1550×g, about 1600×g, about 1650×g, about 1675×g, about 1725×g, about 1750×g, about 1775×g, about 1800×g, about 1825×g, about 1850×g, about 1875×g, about 1900×g, about 1925×g, about 1950×g, or about 1975×g. In an illustrative embodiment, a sample can be centrifuged at a RCF of about 1500×g up to 2000×g, about 1550×g up to 2000×g, about 1600×g up to 2000×g, about 1650×g up to 2000×g, about 1675×g up to 2000×g, about 1700×g up to 2000×g, about 1725×g up to 2000×g, about 1750×g up to 2000×g, about 1775×g up to 2000×g, about 1800×g up to 2000×g, about 1825×g up to 2000×g, about 1850×g up to 2000×g, about 1875×g up to 2000×g, about 1900×g up to 2000×g, about 1925×g up to 2000×g, about 1950×g up to 2000×g, or about 1975×g up to 2000×g.

In an illustrative embodiment, a sample can be centrifuged at a RCF of about 1500×g to about 1900×g, about 1550×g to about 1900×g, about 1600×g to about 1900×g, about 1650×g to about 1900×g, about 1675×g to about 1900×g, about 1700×g to about 1900×g, about 1725×g to about 1900×g, about 1750×g to about 1900×g, about 1775×g to about 1900×g, about 1800×g to about 1900×g, about 1825×g to about 1900×g, about 1850×g to about 1900×g, or about 1875×g to about 1900×g (e.g., a hard spin).

In an illustrative embodiment, a sample can be centrifuged at a RCF of about 1500×g to about 1800×g, about 1550×g to about 1800×g, about 1600×g to about 1800×g, about 1650×g to about 1800×g, about 1675×g to about 1800×g, about 1700×g to about 1800×g, about 1725×g to about 1800×g, about 1750×g to about 1800×g, about 1775×g to about 1800×g, about 1650×g to about 1750×g, about 1675×g to about 1750×g, about 1700×g to about 1750×g, about 1675×g to about 1725×g, or about 1700×g to about 1725×g (e.g., a hard spin).

In an embodiment, a sample, such as a sample that has been subjected to a hard spin, or a sample not yet subjected to centrifugation, can be centrifuged at a RCF that is less than 400×g, which fractionates the blood into a plasma layer and an erythrocyte layer (e.g., a soft spin). In an illustrative embodiment, the plasma layer is a platelet rich plasma layer. In some embodiments, the sample is centrifuged with a "soft spin" at 375×g. In an embodiment, a sample can be centrifuged at about 30×g, about 35×g, about 40×g, about 45×g, about 50×g, about 55×g, about 60×g, about 70×g, about 75×g, about 80×g, about 90×g, about 100×g, about 110×g, about 120×g, about 125×g, about 150×g, about 175×g, or about 200×g.

In an illustrative embodiment, a sample can be centrifuged at a RCF of about 30×g to about 200×g, about 30×g to about 175×g, about 30×g to about 150×g, about 30×g to about 125×g, about 30×g to about 120×g, about 30×g to about 110×g, about 30×g to about 100×g, about 30×g to about 90×g, about 30×g to about 80×g, about 30×g to about 75×g, about 30×g to about 70×g, about 30×g to about 60×g, about 30×g to about 50×g, about 30×g to about 45×g, about 40×g to about 200×g, about 40×g to about 175×g, about 40×g to about 150×g, about 40×g to about 125×g, about 40×g to about 120×g, about 40×g to about 110×g, about 40×g to about 100×g, about 40×g to about 90×g, about 40×g to about 80×g, about 40×g to about 75×g, about 40×g to about 70×g, about 40×g to about 60×g, about 40×g to about 50×g, or about 40×g to about 45×g (e.g., a soft spin).

In an embodiment, a first centrifugation (e.g., a hard spin) can be about 3, about 4, about 5, about 6, about 7, about 8, about 9, about 10, about 11, about 12, about 13, about 14, about 15, about 20, about 25, or about 30 minutes. In an embodiment, a second centrifugation (e.g., a soft spin) can be about 3, about 4, about 5, about 6, about 7, about 8, about 9, about 10, about 11, about 12, about 13, about 14, about 15, about 20, about 25, or about 30 minutes.

In an illustrative embodiment, at least a portion of a plasma layer can be removed after a first centrifugation (e.g., hard spin) and before a second centrifugation (e.g. a soft spin). In an embodiment, at least half, at least 75%, at least 80%, at least 85%, at least 90%, at least 95%, at least 98%, at least 99%, or 100% of the plasma layer is removed. The removed plasma layer can be saved for other purposes, such as diluting a final PRP. In an embodiment after a first hard spin, part of the platelet poor plasma fraction (i.e., that closest to the buffy coat layer), the buffy coat layer, and part of the eyrthrocyte layer (i.e., that closest to the buffy coat layer) is drawn into the second syringe. This can be used a therapeutic fluid. Alternatively, this sample can be centrifuged again such that a top platelet rich plasma fraction and a bottom erythrocyte fraction is obtained. The top platelet rich plasma fraction can be drawn into the third syringe. "Part" of a fraction can be about 5, 10, 20, 30, 40, 50% or more of fraction or about 50, 40, 30, 20, 10, 5% or less of a fraction. In an embodiment, after a first hard spin, the buffy coat fraction is drawn into the second syringe.

In some embodiments, only a single soft spin is used. A soft spin can result in two layers: a PRP layer and an erythrocyte layer. In this embodiment, a leukocyte-reduced PRP (the top fraction) is produced as the therapeutic fluid.

The sample can be further processed beyond the steps of FIG. 22-28 by reattaching the locking cage and second syringe. The plasma and buffy coat can be transferred into the second syringe by moving the plunger of the second syringe away from the first syringe. In some embodiments, the locking cage has viewing windows that allow easier detection of movement of a fraction (e.g. a buffy coat fraction) from the first syringe into the second. Additionally, the translucent material and concave shape of the silicone plug are also of importance in allowing for easier detection of the movement of a fraction like the buffy coat. Once the transfer is complete, the double syringe can be separated by removing the second syringe and locking cage.

In some embodiments, additional fractions of the sample can be drawn into a third syringe body. For example, in some embodiments, the second (soft) spin separates the sample (e.g., part of the platelet poor plasma layer, the buffy coat layer, and part of the erythrocyte layer from the first spin) into two layers: platelet rich plasma and erythrocytes. The third syringe can be pulled back on to extract the platelet rich plasma (top) layer into the third syringe body. In some embodiments, the third syringe body can be used to apply the sample, e.g. platelet rich plasma, to a subject.

Methods of Treatment

Therapeutic fluids produced by compositions and methods described herein can be employed for treatment of human joints, for example, a shoulder joint, a hip joint, an elbow joint, or a knee joint. The therapeutic fluids can be employed for treatment of various cartilage, ligament, or tendon damage or diseases such as, for example: Chondromalacia I°-III°; large and small joints of upper and lower extremities; small vertebral joints; traumatologic cartilage damage; post-operative situations e.g. flake fracture refixation, microfractures and/or cartilage transplantation (autologous cartilage transplantation or osteoarticular transfer device); and tendinosis and ligamentosis.

Therapeutic fluids can also be employed in neurosurgery applications, such as, for example: radiculitis and radiculopathy of the cervical and lumbar spine; syndrome of the vertebral column facets; and other spinal applications, e.g., degeneration of spinal disk and erosive osteochondrosis.

Therapeutic fluids can be clotted before administration using techniques known in the art. Therapeutic fluids may also be applied via a patch, an autograft, or an allograft.

While the compositions and methods are described herein with reference to illustrative embodiments for particular applications, it should be understood that the they are not limited thereto. Those having ordinary skill in the art and access to the teachings provided herein will recognize additional modifications, applications, embodiments and substitution of equivalents within the scope of the disclosure. Accordingly, the compositions and methods are not to be considered as limited by the foregoing description.

Definitions

Unless defined otherwise, all technical and scientific terms used herein have the same meaning as commonly understood to one of ordinary skill in the art. As used herein, the singular forms "a," "an," and "the" include plural referents unless the context clearly dictates otherwise. For example, reference to a "protein" means one or more proteins.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z."

As used herein, a "biological fluid" is a fluid collected from a subject. The subject can be a mammal, including but not limited to human, equine, canine, feline, bovine, porcine, rodent, sheep, or goat. The biological fluids can be autogenic, allogenic, or xenogenic. Biological fluids include, but are not limited to, whole blood, plasma, serum, urine, saliva, mucus, synovial fluid, cerebrospinal fluid, lymphatic fluid, seminal fluid, amniotic fluid, vitreous fluid, as well as fluid collected from cell culture of patient cells, and the like. Biological fluids also include fluids derived from tissue such as, for example, bone, bone marrow, muscle, brain, heart, liver, lung, stomach, small intestine, large intestine, colon, uterus ovary, testis, cartilage, soft tissue, skin, subcutaneous tissue, breast tissue, tissue obtained from other species, patient tissue from surgery, and the like. The tissue can be disrupted. Methods for disrupting tissue are known and include homogenization and enzymatic treatments. Biological fluids also include, for example, bone marrow, fluids obtained from surgery, fluid filtrates, tissue filtrates or fragments, bone chips or fragments obtained during surgery, and the like.

The term "growth factor" as used herein means a bioactive molecule that promotes proliferation of a cell or tissue. Useful growth factors include, but are not limited to, transforming growth factor-alpha (TGF-alpha), transforming growth factor-beta (TGF-beta), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors can also promote differentiation of a cell or tissue. TGF and VEGF, for example, can promote growth and/or differentiation of a cell or tissue. Some growth factors include VEGF, NGFs, PDGF-AA, PDGF-BB, PDGF-AB, FGFb, FGFa, and BGF.

The term "concentrated" refers to a fluid which has been separated by gravity, centrifugation, and/or filtration into various fractions. As used herein, the term "concentrated" is synonymous with the term "enriched," meaning increasing the proportion of desired therapeutic factors in the biological fluid to produce a therapeutic fluid. The term "fraction" refers to the various components into which a biological fluid can be separated by centrifugation, gravitational weight separation and/or filtration. Every fraction can be enriched with a particular fluid component (i.e. concentrated) relative to the other fractions and the original fluid. The concentration process can remove one or more nonessential components from the biological fluid. The concentration process can also remove nonessential components such that the concentrated fraction contains desired components.

The term "therapeutic fluid" means a biological fluid that has been enriched with a higher concentration of one or more therapeutic factors than occurs in the starting biological fluid. As used herein, "therapeutic factors" are components of mammalian biological fluid that can be used as therapeutics, for example, growth factors, differentiation factors, chemotactic factors, adhesion molecules, anti-inflammatories, globulins, and other proteins that can be used as therapeutics such as interleukin-1 receptor antagonist (IL-1ra), thrombin, and alpha-2 macroglobulin. Therapeutic fluids can also include, but are not limited to, autologous conditioned bone marrow concentrate (ACBMC), blood fractions (platelet rich plasma (PRP), platelet poor plasma (PPP), leukocyte-reduced PRP), stem cells (cord blood-derived and bone marrow-derived) for example, concentrated seminal fluid, concentrated spinal fluid, and the like.

As used herein, the terms "treatment" and "treating" refer to the process of administering or applying a therapeutic fluid to a patient at the site of a wound or injury in order to cause or promote healing at the wound or injury site. The concentrated fluid can be autogenic, allogenic, or xenogenic.

The concentrated therapeutic fluid or concentrated biological fluid can be applied in a therapeutically effective amount. For example, an amount sufficient to cause wound or injury healing when a therapeutic fluid is applied to a wound or injury site would be a therapeutically effective amount.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1

A sample comprised of a mixture of whole blood and bone marrow from a single donor was subjected to a two syringe methodology and a three syringe methodology. Initially, the whole blood and bone marrow mixture was tested for white blood cell amount, red blood cell amount, hemocrit percentage, platelet amount, hematopoietic progenitor cell amount, colony forming units-fibroblast amount, and percentage of mononuclear cells. In a two syringe method the mixture of whole blood and bone marrow was introduced into a first syringe having a first body with a first diameter of a device. The device had a second syringe having a second body with a second diameter smaller than the first diameter nested within the first syringe. The second syringe had a plunger nested within the second body. A locking support cage comprising a tubular body having an aperture, and at least one ridge was disposed on an outer surface of the tubular body surrounding the second syringe. A locking clip was configured to surround the locking cage and to be fastened around the finger grips of the first syringe, wherein the locking clip comprised an inner surface configured to interact with the at least one ridge of the locking cage so as to prevent regression of the plunger during extension. The first syringe was centrifuged so that three fractions were obtained: a platelet poor plasma layer (top), a buffy coat layer (middle), and an erythrocyte layer (bottom). A small portion of the platelet poor plasma layer, all of the buffy coat layer, and a small portion of the erythrocyte layer was transferred from the first syringe to the second syringe. This fraction in the second syringe was analyzed for white blood cell amount, red blood cell amount, hemocrit percentage, platelet amount, hematopoietic progenitor cell amount, colony forming units-fibroblast amount, and percentage of mononuclear cells. The results are shown in Table 1. The recovery percentages were calculated by taking (final concentration×final volume)/(input concentration×input volume).

In the three syringe method the device comprised a first syringe having a first body with a first diameter; a second syringe having a second body with a second diameter smaller than the first diameter nested within the first syringe; a third syringe having a third body with a third diameter smaller than the second diameter nested within the second syringe, and a plunger nested within the third body. The device also comprised a locking support cage comprising a tubular body having an aperture, and at least one ridge disposed on an outer surface of the tubular body, wherein the locking support cage surrounded the second syringe. A locking clip was configured to surround the locking cage and to be fastened around the finger grips of the first syringe, wherein the locking clip comprised an inner surface configured to interact with the at least one ridge of the locking cage so as to prevent regression of the plunger during extension. A sample comprised of a mixture of whole blood and bone marrow was introduced into the first syringe. The first syringe was centrifuged so that three fractions were obtained: a platelet poor plasma layer (top), a buffy coat layer (middle), and an erythrocyte layer (bottom). A small portion of the platelet poor plasma layer, all of the buffy coat layer, and a small portion of the erythrocyte layer was transferred from the first syringe to the second syringe. The second and third syringes were centrifuged to form two layers within the second syringe: a platelet rich plasma layer (top) and an erythrocyte layer (bottom). The platelet rich plasma layer was drawn into the third syringe and analyzed. The results are shown in Table 1.

| | Final volume (ml) | WBC (k/μl) | RBC (M/μl) | HCT % | PLT (k/μl) | HPC (k/μl) | CFU-F (#/ml) | MNC % |
|---|---|---|---|---|---|---|---|---|
| Baseline | N/A | 6.7 | 4.8 | 45.2 | 151.4 | 0.000 | 11.3 | 32.3 |
| Two syringe method | 15 | 16.4 | 4.7 | 45.7 | 355.3 | 0.0001 | 109.1 | 37.6 |
| Three syringe method | 4 | 34.8 | 1.7 | 17.2 | 874.7 | 0.0001 | 348.5 | 39.3 |

| | WBC % | RBC % | PLT % |
|---|---|---|---|
| Two syringe method recovery | 61% | 24% | 59% |
| Three syringe method recovery | 35% | 2% | 39% |

What is claimed is:

1. A device for controlling the movement of a syringe plunger within an outer syringe comprising: a locking support cage comprising a tubular body having an aperture that is configured to surround the syringe plunger and to fit within the outer syringe, and at least one ridge disposed on an outer surface of the tubular body; and
   a locking clip configured to surround the locking support cage and a finger grip of the outer syringe, wherein the locking clip comprises an inner surface configured to interact with the at least one ridge so as to prevent regression of the syringe plunger during extension of the syringe plunger from the outer syringe.

2. The device of claim 1, wherein the at least one ridge is configured so that one surface of the at least one ridge forms an oblique angle relative to the tubular body of the locking support cage.

3. The device of claim 1, wherein the locking clip is hinged.

4. The device of claim 1, wherein the locking clip comprises protrusions configured to catch on the at least one ridge of the locking support cage.

5. The device of claim 1, further comprising the outer syringe containing:
   a swabbable valve;
   a plug comprising an aperture and at least one concave surface; and
   a gasket configured to interact with the locking support cage, the swabbable valve, and the plug;
   wherein the gasket interacts with the locking support cage and the swabbable valve on one surface and interacts with the plug on an opposite surface; and
   wherein the at least one concave surface of the plug is opposite a surface that interacts with the gasket.

6. The device of claim 5, wherein the at least one concave surface on the gasket has a conical recess.

7. A device for controlled positioning of a plunger comprising:
   a) a first syringe having a first body with a first diameter;
   b) a second syringe nested within the first syringe, wherein the second syringe comprises a second body with a second diameter smaller than the first diameter; and
   c) the plunger nested within the second body;
   d) a locking support cage comprising a tubular body having an aperture, and at least one ridge disposed on an outer surface of the tubular body, wherein the locking support cage surrounds the second syringe, and fits within the first body; and
   e) a locking clip configured i) to surround the locking support cage and to be fastened around finger grips of the first syringe, and ii) to interact with the at least one ridge of the locking support cage via an inner surface so as to prevent regression of the plunger during extension of the plunger.

8. The device of claim 7, wherein the at least one ridge is configured so that one surface of the at least one ridge forms an oblique angle relative to the tubular body of the locking support cage.

9. The device of claim 7, wherein the locking clip is hinged.

10. The device of claim 7, wherein the locking clip comprises protrusions configured to catch on the at least one ridge of the locking support cage.

11. The device of claim 7, further comprising within the first body:
    a swabbable valve;
    a plug comprising an aperture and at least one concave surface; and
    a gasket configured to interact with the locking support cage, the swabbable valve, and the plug;
    wherein the gasket interacts with the locking support cage and the swabbable valve on one surface and interacts with the plug on an opposite surface; and
    wherein the at least one concave surface of the plug is opposite a surface that interacts with the gasket.

12. The device of claim 7, further comprising:
    a male or female Luer connector attached to the first syringe; and a bone marrow aspiration needle attached to the male or female Luer connector.

* * * * *